United States Patent

Bruneau et al.

Patent Number: 5,407,945
Date of Patent: Apr. 18, 1995

[54] PYRAN DERIVATIVES AND THEIR USE AS INHIBITORS OF 5-LIPOXYGENASE

[75] Inventors: Pierre A. R. Bruneau, Ludes, France; Robert I. Dowell, Congleton; David Waterson, Macclesfield, both of England

[73] Assignees: Imperial Chemical Industries, Inc., London, England; ICI-Pharma, Cergy Cedex, France

[21] Appl. No.: 99,435

[22] Filed: Jul. 30, 1993

Related U.S. Application Data

[60] Division of Ser. No. 12,810, Feb. 2, 1993, Pat. No. 5,254,581, which is a continuation of Ser. No. 717,509, Jun. 19, 1991, abandoned.

[30] Foreign Application Priority Data

Jun. 21, 1990 [EP] European Pat. Off. ........... 90401755

[51] Int. Cl.$^6$ ..................... A61K 31/47; C07D 405/12
[52] U.S. Cl. .................... 514/312; 514/314; 546/153; 546/157; 546/160; 546/175; 546/176; 546/177; 546/178; 546/180
[58] Field of Search ........................ 514/311, 312, 314; 546/153, 155, 156, 157

[56] References Cited

U.S. PATENT DOCUMENTS

| | | | |
|---|---|---|---|
| 2,242,575 | 5/1941 | Eisleb | 269/333 |
| 3,422,102 | 1/1969 | Morren | 260/247.2 |
| 3,661,917 | 5/1972 | Kaiser et al. | 260/293.73 |
| 3,743,737 | 7/1973 | Kaiser et al. | 424/267 |
| 4,567,184 | 1/1986 | Musser et al. | 514/277 |
| 4,625,034 | 11/1986 | Neiss et al. | 514/152 |
| 4,631,287 | 12/1986 | Chakraborty et al. | 514/307 |
| 4,725,619 | 2/1986 | Chakraborty et al. | 514/442 |
| 4,728,668 | 3/1988 | Chakraborty et al. | 514/464 |

(List continued on next page.)

FOREIGN PATENT DOCUMENTS

| | | |
|---|---|---|
| 2023829 | 2/1991 | Canada . |
| 0110405 | 6/1984 | European Pat. Off. . |
| 0181568 | 5/1986 | European Pat. Off. . |
| 0190722 | 8/1986 | European Pat. Off. . |
| 0200101 | 12/1986 | European Pat. Off. . |
| 0271287 | 6/1988 | European Pat. Off. . |
| 0349062 | 6/1989 | European Pat. Off. . |
| 1382753 | 11/1964 | France . |

*Primary Examiner*—C. Warren Ivy
*Assistant Examiner*—Evelyn Huang
*Attorney, Agent, or Firm*—Cushman Darby & Cushman

[57] ABSTRACT

The invention concerns a cyclic ether derivative of the formula I $$Ar^1-A^1-X^1-Ar^2-\underset{\underset{R^3}{|}}{\overset{\overset{R^1}{|}}{C}}-R^2 \qquad I$$

wherein $Ar^1$ is optionally substituted phenyl, naphthyl or a 9- or 10-membered bicyclic heterocyclic moiety;
$A^1$ is a direct link to $X^1$ or (1-3C)alkylene;
$X^1$ is oxy, thio, sulphinyl, sulphonyl or imino;
$Ar^2$ is optionally substituted phenylene or pyridylene;
$R^1$ includes hydrogen, (1-4C)alkyl, (1-4C)alkoxycarbonyl and (1-4C)alkylthio; and
$R^2$ and $R^3$ together form a group of the formula $-A^2-X^2-A^3-$ which, together with the carbon atom to which $A^2$ and $A^3$ are attached, defines a ring having 5 to 7 ring atoms, wherein each of $A^2$ and $A^3$ is (1-3C)alkylene and $X^2$ is oxy, thio, sulphinyl or sulphonyl;

or a pharmaceutically-acceptable salt thereof.

The compounds of the invention are inhibitors of the enzyme 5-lipoxygenase.

9 Claims, No Drawings

U.S. PATENT DOCUMENTS

| | | | |
|---|---|---|---|
| 4,794,188 | 12/1988 | Musser et al. | 546/152 |
| 4,839,369 | 6/1989 | Youssefyeh et al. | 514/314 |
| 4,876,346 | 10/1989 | Musser et al. | 546/172 |
| 4,918,081 | 4/1990 | Huang et al. | 514/311 |
| 4,920,130 | 4/1990 | Huang et al. | 514/311 |
| 4,920,131 | 4/1990 | Huang et al. | 514/311 |
| 4,920,132 | 4/1990 | Huang et al. | 514/314 |
| 4,920,133 | 4/1990 | Huang et al. | 514/314 |
| 4,929,626 | 5/1990 | Mohrs | 514/311 |
| 4,970,215 | 11/1990 | Mohrs | 514/311 |
| 5,089,495 | 2/1992 | Crawley et al. | 514/253 |
| 5,089,513 | 2/1992 | Bird et al. | 514/365 |
| 5,098,930 | 3/1992 | Edwards et al. | 514/459 |
| 5,098,932 | 3/1992 | Hamon | 514/462 |
| 5,105,020 | 4/1992 | Girodeau | 568/633 |
| 5,126,365 | 6/1992 | Bird et al. | |
| 5,132,328 | 7/1992 | Girodeau | 514/716 |
| 5,134,148 | 7/1992 | Crawley | 514/312 |
| 5,137,913 | 8/1992 | Bird et al. | 514/467 |
| 5,179,115 | 1/1993 | Bruneau et al. | 514/387 |
| 5,196,419 | 3/1993 | Crawley | 514/241 |
| 5,196,422 | 3/1993 | Bird et al. | 514/252 |
| 5,202,326 | 4/1993 | Crawley et al. | 514/255 |
| 5,208,259 | 5/1993 | Bird et al. | 514/460 |
| 5,214,069 | 5/1993 | Girodeau | 514/706 |
| 5,214,070 | 5/1993 | Bird et al. | 514/708 |
| 5,217,969 | 6/1993 | Bruneau et al. | 514/230.5 |
| 5,217,977 | 6/1993 | Crawley et al. | 514/311 |
| 5,217,978 | 6/1993 | Bird | 514/312 |
| 5,219,881 | 6/1993 | Hamon | 514/452 |
| 5,221,677 | 6/1993 | Crawley et al. | 514/309 |
| 5,225,438 | 7/1993 | Dowell et al. | 514/459 |
| 5,232,930 | 8/1993 | Kingston et al. | 514/314 |

PYRAN DERIVATIVES AND THEIR USE AS INHIBITORS OF 5-LIPOXYGENASE

This is a division of application No. 08/012,810, filed Feb. 2, 1993, now U.S. Pat. No. 5,254,581, which was a FWC of 07/717,509, filed Jun. 19, 1991, now abandoned.

This invention concerns novel cyclic ether derivatives and more particularly novel cyclic ether derivatives which are inhibitors of the enzyme 5-lipoxygenase (hereinafter referred to as 5-LO). The invention also concerns processes for the manufacture of said cyclic ether derivatives and novel pharmaceutical compositions containing them. Also included in the invention is the use of said cyclic ether derivatives in the treatment of various inflammatory and/or allergic diseases in which the direct or indirect products of 5-LO catalysed oxidation of arachidonic acid are involved, and the production of new medicaments for such use.

As stated above the cyclic ether derivatives described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100–103. The leukotrienes and their metabolites have been implicated in the production and development of various inflammatory and allergic diseases such as arthritic diseases, asthma, allergic rhinitis, atopic dermatitis, psoriasis, cardiovascular and cerebrovascular disorders and inflammatory bowel disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

We have now discovered that certain cyclic ether derivatives are effective as inhibitors of the enzyme 5-LO and thus of leukotriene biosyntheses. Thus, such compounds are of value as therapeutic agents in the treatment of, for example, allergic conditions, psoriasis, asthma, cardiovascular and cerebrovascular disorders, and/or inflammatory and arthritic conditions, mediated alone or in part by one or more leukotrienes.

According to the invention there is provided a cyclic ether derivative of the formula I (set out hereinafter) wherein $Ar^1$ is phenyl or naphthyl, or a 9- or 10-membered bicyclic heterocyclic moiety containing one or two nitrogen heteroatoms and optionally containing a further heteroatom selected from nitrogen, oxygen and sulphur, and $Ar^1$ may optionally bear up to five substituents selected from amino, halogeno, hydroxy, cyano, oxo, thioxo, (1-4C)alkyl, (1-4C)alkoxy, (1-4C)alkylthio, (1-4C)alkylsulphinyl, (1-4C)alkylsulphonyl, (1-4C)alkylamino, di-[(1-4C)alkyl]amino, (2-4C)alkanoyl, fluoro-(1-4C)alkyl, cyano-(1-4C)alkyl, phenyl, benzoyl and phenyl-(1-4C)alkyl, and wherein said phenyl, benzoyl or phenyl-(1-4C)alkyl substituents may optionally bear a substituent selected from halogeno, (1-4C)alkyl and (1-4C)alkoxy;

wherein $A^1$ is a direct link to $X^1$ or is (1-3C)alkylene;

wherein $X^1$ is oxy, thio, sulphinyl, sulphonyl or imino;

wherein $Ar^1$ is phenylene which may optionally bear one or two substituents selected from halogeno, hydroxy, amino, nitro, cyano carbamoyl, ureido, (1-4C)alkyl, (1-4C)alkoxy, (1-4C)alkylamino, di-[(1-4C)alkyl]amino, fluoro-(1-4C)alkyl and (2-4C)alkanoylamino; or $Ar^2$ is pyridylene;

wherein $R^1$ is (1-4C)alkylthio, (1-4C)alkylsulphinyl, (1-4C)alkylsulphonyl, (1-4C)alkylamino or di-[(1-4C)alkyl]amino, or $R^1$ is hydrogen, formyl, cyano, carbamoyl, (1-4C)alkyl, (1-4C)alkoxycarbonyl, N-(1-4C)alkylcarbamoyl, N,N-di-[(1-4C)alkyl]carbamoyl, hydroxy-(1-4C)alkyl, fluoro-(1-4C)alkylthio, (2-4C)alkanoyl or (1-4C)alkoxy-(1-4C)alkyl; and wherein $R^2$ and $R^3$ together form a group of the formula —$A^2$—$X^2$—$A^3$— which, together with the carbon atom to which $A^2$ and $A^3$ are attached, defines a ring having 5 to 7 ring atoms, wherein $A^2$ and $A^3$, which may be the same or different, each is (1-3C)alkylene and $X^2$ is oxy, thio, sulphinyl or sulphonyl, and which ring may bear one, two or three substituents, which may be the same or different, selected from hydroxy, (1-4C)alkyl and (1-4C)alkoxy;

or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of the formula I defined above may exhibit the phenomenon of tautomerism and any formula drawing presented herein may represent only one of the possible tautomeric forms, the invention includes in its definition any tautomeric form of a compound of the formula I which possesses the property of inhibiting 5-LO and is not to be limited merely to any one tautomeric form utilised within the formulae drawings.

It is further to be understood that, insofar as certain of the compounds of formula I defined above may exist in optically active or racemic forms by virtue of one or more substituents containing an asymmetric carbon atom, the invention includes in its definition any such optically active or racemic form which possesses the property of inhibiting 5-LO. The synthesis of optically active forms may be carried out by standard techniques of organic chemistry veil known in the art, for example by synthesis from optically active starting materials or by resolution of a racemic form. Similarly, inhibitory properties against 5-LO may be evaluated using the standard laboratory techniques referred to hereinafter.

According to a further feature of the invention there is provided a cyclic ether derivative of the formula I wherein $Ar^1$ is phenyl or naphthyl, or a 9- or 10-membered bicyclic heterocyclic moiety containing one or two nitrogen heteroatoms and optionally containing a further heteroatom selected from nitrogen, oxygen and sulphur, and $Ar^1$ may optionally bear up to five substituents selected from amino, halogeno, hydroxy, cyano, oxo, thioxo, (1-4C)alkyl, (1-4C)alkoxy, (1-4C)alkylthio, (1-4C)alkylsulphinyl, (1-4C)alkylsulphonyl, (1-4C)alkylamino, di-[(1-4C)alkyl]amino, (2-4C)alkanoyl, fluoro-(1-4C)alkyl, cyano-(1-4C)alkyl, phenyl, benzoyl and phenyl-(1-4C)alkyl, and wherein said phenyl, benzoyl or phenyl-(1-4C)alkyl substituents may optionally bear a substituent selected from halogeno, (1-4C)alkyl and (1-4C)alkoxy;

wherein $A^1$ is a direct link to $X^1$ or is (1-3C)alkylene;
wherein $X^1$ is oxy, thio, sulphinyl, sulphonyl or imino;
wherein $Ar^2$ is phenylene which may optionally bear one or two substituents selected from halogeno, hydroxy, amino, nitro, cyano carbamoyl, ureido, (1-4C)alkyl, (1-4C)alkoxy, (1-4C)alkylamino, di-[(1-4C)alkyl]amino, fluoro-(1-4C)alkyl and (2-4C)alkanoylamino; or
$Ar^2$ is pyridylene;
wherein $R^1$ is (1-4C)alkylthio, (1-4C)alkylsulphinyl, (1-4C)alkylsulphonyl, (1-4C)alkylamino or di-[(1-4C)alkyl]amino, or $R^1$ is cyano, carbamoyl, (1-4C)alkoxycarbonyl, N-(1-4C)alkylcarbamoyl, N,N-di-i(1-4C)alkyl]carbamoyl, hydroxy-(1-4C)alkyl or (1-4C)alkoxy-(1-4C)alkyl; and
wherein $R^2$ and $R^3$ together form a group of the formula —$A^2$—$X^2$—$A^3$— which, together with the carbon atom to which $A^2$ and $A^3$ are attached, defines a ring having 5 to 7 ring atoms, wherein $A^2$ and $A^3$ which may be the same or different each is (1-3C)alkylene and $X^2$ is oxy, thio, sulphinyl or sulphonyl, and which ring may bear one, two or three substituents, which may be the same or different, selected from hydroxy, (1-4C)alkyl and (1-4C)alkoxy;

or a pharmaceutically-acceptable salt thereof.

Suitable values for the generic terms referred to above include those set out below.

A suitable value for $Ar^1$ when it is a 9- or 10-membered bicyclic heterocyclic moiety containing one or two nitrogen heteroatoms and optionally containing a further heteroatom selected from nitrogen, oxygen and sulphur is, for example, a 9- or 10-membered benzo-fused heterocyclic moiety such as indolyl, isoindolyl, benzimidazolyl, 1H-indazolyl, benzoxazolyl, benzothiazolyl, quinolyl, isoquinolyl, cinnolinyl, quinazolinyl, quinoxalinyl, 4H-1,4-benzoxazinyl or 4H-1,4-benzothiazinyl, or a hydrogenated derivative thereof such as indolinyl, 2,3-dihydrobenzimidazolyl, 2,3-dihydrobenzoxazolyl, 2,3-dihydrobenzothiazolyl, 1,2-dihydroquinolyl, 1,2,3,4-tetrahydroquinolyl, 1,2-dihydroisoquinolyl, 2,3-dihydro-4H-1,4-benzoxazinyl or 2,3-dihydro-4H-1,4-benzothiazinyl; or, for example, a 9- or 10-membered pyrido-fused heterocyclic moeity such as 1H-pyrrolo[2,3-b]pyridyl, imidazo[4,5-b]pyridyl, 1,7-naphthyridinyl, 1,8-naphthyridinyl, pyrido[2,3-d]pyrimidinyl, pyrido[2,3-b]pyrazinyl, 4H-pyrido[3,2-b][1,4]oxazinyl and 4H-pyrido[3,2-b][1,4]thiazinyl, or a hydrogenated derivative thereof.

The heterocyclic moiety may be attached through any available position including from either of the two rings of the bicyclic heterocyclic moiety and including through an available nitrogen atom. The heterocyclic moiety may bear a suitable substituent such as, for example, a (1-4C)alkyl, phenyl, benzoyl or phenyl-(1-4C)alkyl substituent on an available nitrogen atom.

Suitable values for substituents which may be present on $Ar^1$ or $Ar^2$, or on a phenyl, benzoyl or phenyl-(1-4C)alkyl substituent on $Ar^1$, include, for example:

for halogeno: fluoro, chloro, bromo and iodo;
for (1-4C)alkyl: methyl, ethyl, propyl, isopropyl, butyl, isobutyl, sec-butyl and tert-butyl;
for (1-4C)alkoxy: methoxy, ethoxy, propoxy, isopropoxy and butoxy;
for fluoro-(1-4C)alkyl: fluoromethyl, difluoromethyl, trifluoromethyl, 2-fluoroethyl, 2,2,2-trifluoroethyl and pentafluoroethyl;
for (1-4C)alkylamino: methylamino, ethylamino, propylamino and butylamino;
for di-[(1-4C)alkyl]amino: dimethylamino, diethylamino and dipropylamino.

Suitable values for substituents which may be present on $Ar^1$ include, for example:

for (1-4C)alkythio: methylthio, ethylthio, propylthio, isopropylthio and butylthio;
for (1-4C)alkylsulphinyl: methylsulphinyl, ethylsulphinyl, propylsulphinyl, isopropylsulphinyl and butylsulphinyl;
for (1-4C)alkylsulphonyl: methylsulphonyl, ethylsulphonyl, propylsulphonyl, isopropylsulphonyl and butylsulphonyl;
for (2-4C)alkanoyl: acetyl, propionyl and butyryl;
for cyano-(1-4C)alkyl: cyanomethyl, 1-cyanoethyl, 2-cyanoethyl, 3-cyanopropyl and 2-cyanoprop-2-yl;
for phenyl-(1-4C)alkyl: benzyl, phenethyl and 3-phenylpropyl.

A suitable value for $A^1$ when it is (1-3C)alkylene is, for example, methylene, ethylene or trimethylene.

A suitable value for $Ar^2$ when it is phenylene is, for example 1,3-phenylene or 1,4-phenylene.

A suitable value for $Ar^2$ when it is pyridylene is, for example 3,5- or 2,6-pyridylene.

A suitable value for a (2-4C)alkanoylamino substituent which may be present on $Ar^2$ is, for example, acetamido, propionamido or butyramido.

A suitable value for $R^1$ when it is (1-4C)alkylthio is, for example, methylthio, ethylthio, propylthio, isopropylthio or butylthio; when it is (1-4C)alkylsulphinyl is, for example, methylsulphinyl, ethylsulphinyl, propylsulphinyl, isopropylsulphinyl or butylsulphinyl; when it is (1-4C)alkylsulphonyl is, for example, methylsulphonyl, ethylsulphonyl, propylsulphonyl, isopropylsulphonyl and butylsulphonyl; when it is (1-4C)alkylamino is, for example, methylamino, ethylamino, propylamino, isopropylamino or butylamino; and when it is di-[(1-4C)alkyl]amino is, for example, dimethylamino, diethylamino or dipropylamino.

A suitable value for $R^1$ when it is (1-4C)alkyl is, for example, methyl, ethyl, propyl, isopropyl, butyl or isobutyl; when it is (1-4C)alkoxycarbonyl is, for example, methoxycarbonyl, ethoxycarbonyl, propoxycarbonyl, isopropoxycarbonyl or butoxycarbonyl; when it is N-(1-4C)alkylcarbamoyl is, for example, N-methylcarbamoyl, N-ethylcarbamoyl or N-propylcarbamoyl; when it is N,N-di-[(1-4C)alkyl]carbamoyl is, for example, N,N-dimethylcarbamoyl, N,N-diethylcarbamoyl or N,N-dipropylcarbamoyl; when it is hydroxy-(1-4C)alkyl is, for example, hydroxymethyl, 1-hydroxyethyl, 2-hydroxyethyl, 2-hydroxypropyl or 3-hydroxypropyl; when it is fluoro-(1-4C)alkylthio is, for example, fluoromethylthio, difluoromethylthio, trifluoromethylthio, 2-fluoroethylthio, 2,2,2-trifluoroethylthio or pentafluoroethylthio; when it is (2-4C)alkanoyl is, for example, acetyl, propionyl or butyryl; and when it is (1-4C)alkoxy-(1-4C)alkyl is, for example, methoxymethyl, ethoxymethyl, 1-methoxyethyl, 1-ethoxyethyl, 2-methoxyethyl, 2-ethoxyethyl, 3-methoxypropyl or 3-ethoxypropyl.

When $R^2$ and $R^3$ together form a group of the formula —$A^2$—$X^2$—$A^3$— which, together with the carbon atom to which $A^2$ and $A^3$ are attached, defines a ring having 5 to 7 ring atoms then a suitable value for $A^2$ or $A^3$, which may be the same or different, when each is (1-3C)alkylene is, for example, methylene, ethylene or trimethylene. Suitable values for the substituents which may be present on said 5- to 7-membered ring include for example:

for (1-4C)alkyl: methyl, ethyl, propyl, isopropyl, butyl and isobutyl;

for (1-4C)alkoxy: methoxy, ethoxy, propoxy, isopropoxy and butoxy.

A suitable pharmaceutically-acceptable salt of a novel compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a novel compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention are, for example, cyclic ether derivatives of the formula I wherein:

(a) $Ar^1$ is phenyl or naphthyl which may optionally bear one, two or three substituents selected from any of those substituents on $Ar^1$ defined hereinbefore other than oxo and thioxo;

(b) $Ar^1$ is phenyl or naphth-2-yl which may optionally bear one or two substituents selected from fluoro, chloro, methyl, ethyl, isopropyl, tert-butyl, methoxy, trifluoromethyl, 2-cyanoprop-2-yl, phenyl and benzoyl, and wherein said phenyl or benzoyl substituents may optionally bear a substituent selected from chloro, methyl and methoxy; and $A^1$, $X^1$, $Ar^2$, $R^1$, $R^2$ and $R^3$ have any of the meanings defined hereinbefore;

(c) $Ar^1$ is a 9- or 10-membered benzo-fused heterocyclic moiety containing one or two nitrogen heteroatoms and optionally containing a futher heteroatom selected from oxygen and sulphur, which heterocyclic moiety may optionally bear one or two oxo or thioxo substituents and up to three further substituents selected from any of those substituents on $Ar^1$ defined hereinbefore other than oxo or thioxo; and $A^1$, $X^1$, $Ar^2$, $R^1$, $R^2$ and $R^3$ have any of the meanings defined hereinbefore;

(d) $Ar^1$ is indolyl, indolinyl, benzimidazolyl, 2,3-dihydrobenzimidazolyl, benzoxazolyl, 2,3-dihydrobenzoxazolyl, benzothiazolyl, 2,3-dihydrobenzothiazinyl, quinolyl, 1,2-dihydroquinolyl, isoquinolyl, 1,2-dihydroisoquinolyl, quinoxalinyl, 2,3-dihydro-4H-1,4-benzoxazinyl or 2,3-dihydro-4H-1,4-benzothiazinyl, which may optionally bear one or two oxo or thioxo substituents and up to three further substituents selected from any of those substituents on $Ar^1$ defined hereinbefore other than oxo or thioxo; and $A^1$, $X^1$, $Ar^2$, $R^1$, $R^2$ and $R^3$ have any of the meanings defined hereinbefore;

(e) $Ar^1$ is 2-indolyl, 3-indolyl, 5-indolyl, 6-indolyl, 2-benzimidazolyl, 5-benzimidazolyl, 6-benzimidazolyl, 2-benzoxazolyl, 5-benzoxazolyl, 6-benzoxazolyl, 2-benzothiazolyl, 5-benzothiazolyl, 6-benzothiazolyl, 2-quinolyl, 3-quinolyl, 6-quinolyl, 7-quinolyl, 3-isoquinolyl, 6-isoquinolyl, 7-isoquinolyl, 2-quinoxalinyl, 6-quinoxalinyl, 4H-1,4-benzoxazin-6-yl or 4H-1,4-benzothiazin-6-yl, which may optionally bear one or two substituents selected from any of those substituents on $Ar^1$ defined hereinbefore other than oxo or thioxo; and $A^1$, $X^1$, $Ar^2$, $R^1$, $R^2$ and $R^3$ have any of the meanings defined hereinbefore;

(f) $Ar^1$ is 2-oxoindolinyl, 2,3-dioxoindolinyl, 2-oxo-2,3-dihydrobenzimidazolyl, 2-oxo-2,3-dihydrobenzoxazolyl, 2-oxo-2,3-dihydrobenzothiazolyl, 2-oxo-1,2-dihydroquinolinyl, 3-oxo-2,3-dihydro-4H-1,4-benzoxazinyl or 3-oxo-2,3-dihydro-4H-1,4-benzothiazinyl, or the corresponding thioxo derivatives thereof, which may optionally bear up to three substituents selected from any of those substituents on $Ar^1$ defined hereinbefore other than oxo or thioxo; and $A^1$, $X^1$, $Ar^2$, $R^1$, $R^2$ and $R^3$ have any of the meanings defined hereinbefore;

(g) $Ar^1$ is 2-oxoindolin-5-yl, 2,3-dioxoindolin-5-yl, 2-oxo-2,3-dihydrobenzimidazol-5-yl, 2-oxo-2,3-dihydrobenzoxazol-5-yl, 2-oxo-2,3-dihydrobenzothiazol-5-yl, 2-oxo-1,2-dihydroquinolin-3-yl, 2-oxo-1,2-dihydroquinolin-6-yl, 2-oxo-1,2-dihydroquinolin-7-yl, 3-oxo-2,3-dihydro-4H-1,4-benzoxazin-7-yl or 3-oxo-2,3-dihydro-4H-1,4-benzothiazol-7-yl, which may optionally bear up to three substituents selected from any of those substituents on $Ar^1$ defined hereinbefore other than oxo or thioxo; and $A^1$, $X^1$, $Ar^2$, $R^1$, $R^2$ and $R^3$ have any of the meanings defined hereinbefore;

(h) $A^1$ is a direct link to $X^1$, and $X^1$ is oxy, thio, sulphinyl or sulphonyl; and $Ar^1$, $Ar^2$, $R^1$, $R^2$ and $R^3$ have any of the meanings defined hereinbefore;

(i) $A^1$ is methylene and $X^1$ is oxy, thio, sulphinyl or sulphonyl; and $Ar^1$, $Ar^2$, $R^1$, $R^2$ and $R^3$ have any of the meanings defined hereinbefore;

(j) $Ar^2$ is 1,3-phenylene or 1,4-phenylene which may optionally bear one or two substituents selected from fluoro, chloro, hydroxy, amino, nitro, ureido, methyl, methoxy, methylamino, dimethylamino, trifluoromethyl and acetamido; and $Ar^1$, $A^1$, $X^1$, $R^1$, $R^2$ and $R^3$ have any of the meanings defined hereinbefore;

(k) $Ar^2$ is 3,5-pyridylene; and $Ar^1$, $A^1$, $X^1$, $R^1$, $R^2$ and $R^3$ have any of the meanings defined hereinbefore;

(l) $R^1$ is methylthio, ethylthio, propylthio, methylsulphinyl, ethylsulphinyl, propylsulphinyl, methylsulphonyl, ethylsulphonyl, propylsulphonyl, methylamino, ethylamino, dimethylamino or diethylamino; and $Ar^1$, $A^1$, $X^1$, $Ar^2$, $R^2$ and $R^3$ have any of the meanings defined hereinbefore;

(m) $R^1$ is cyano, carbamoyl, methoxycarbonyl, ethoxycarbonyl, propoxycarbonyl, N-methylcarbamoyl, N-ethylcarbamoyl, N,N-dimethylcarbamoyl, N,N-diethylcarbamoyl, hydroxymethyl, 2-hydroxyethyl, 3-hydroxypropyl, methoxymethyl, ethoxymethyl, 2-methoxyethyl, 2-ethoxyethyl, 3-methoxypropyl or 3-ethoxypropyl; and $Ar^1$, $A^1$, $X^1$, $Ar^2$, $R^2$ and $R^3$ have any of the meanings defined hereinbefore; or (n) $R^1$ is hydrogen, formyl, cyano, methyl, ethyl, propyl, methoxycarbonyl, ethoxycarbonyl, propoxycarbonyl, hydroxymethyl, 1-hydroxyethyl, 2-hydroxyethyl, 2,2,2-trifluoroethyl, acetyl, propionyl, methoxymethyl, ethoxymethyl, 2-methoxyethyl or 2-ethoxyethyl; and $Ar^1$, $A^1$, $X^1$, $Ar^2$, $R^2$ and $R^3$ have any of the meanings defined hereinbefore;

(o) $R^2$ and $R^3$ together form a group of the formula —$A^2$—$X^2$—$A^3$— which, together with the carbon atom to which $A^2$ and $A^3$ are attached, defines a ring having 5 to 7 ring atoms wherein $A^2$ and $A^3$, which may be the same or different, each is methylene, ethylene or trimethylene and $X^2$ is oxy, and which ring may bear one or two substituents selected from hydroxy, methyl, ethyl, propyl, methoxy and ethoxy; and $Ar^1$, $A^1$, $X^1$, $Ar^2$ and $R^1$ have any of the meanings defined hereinbefore.

or a pharmaceutically-acceptable salt thereof.

A preferred compound of the invention comprises a cyclic ether derivative of the formula I wherein $Ar^1$ is phenyl or naphth-2-yl which may optionally bear one or two substituents selected from fluoro, chloro, methyl, ethyl, isopropyl, tert-butyl, methoxy, trifluoromethyl, 2-cyanoprop-2-yl, phenyl and benzoyl and wherein said phenyl or benzoyl substituents may optionally bear a substituent selected from chloro, methyl and methoxy;

$A^1$ is a direct link to $X^1$, or is methylene;

$X^1$ is oxy, thio, sulphinyl or sulphonyl;

$Ar^2$ is 1,3-phenylene or 1,4-phenylene which may optionally bear one or two substituents selected from fluoro, chloro, hydroxy, amino, nitro, ureido, methoxy, dimethylamino, trifluoromethyl and acetamido; or $Ar^2$ is 3,5-pyridylene;

$R^1$ is methylthio, ethylthio, propylthio, methylsulphinyl, ethylsulphinyl, propylsulphinyl, methylsulphonyl, ethylsulphonyl, propylsulphonyl, methylamino, ethylamino, dimethylamino or diethylamino, or $R^1$ is cyano, carbamoyl, methoxycarbonyl, ethoxycarbonyl, propoxycarbonyl, N-methylcarbamoyl, N-ethylcarbamoyl, N,N-dimethylcarbamoyl, N,N-diethylcarbamoyl, hydroxymethyl, 2-hydroxyethyl, 3-hydroxypropyl, methoxymethyl, ethoxymethyl, 2-methoxyethyl, 2-ethoxyethyl, 3-methoxypropyl or 3-ethoxypropyl; and $R^2$ and $R^3$ together form a group of the formula —$A^2$—$X^2$—$A^3$— which, together with the carbon atom to which $A^2$ and $A^3$ are attached, defines a ring having 5 or 6 ring atoms, wherein $A^2$ is ethylene, $A^3$ is methylene or ethylene, and $X^2$ is oxy, and which ring may bear one or two substituents selected from methyl and ethyl;

or a pharmaceutically-acceptable salt thereof.

A further preferred compound of the invention comprises a cyclic ether derivative of the formula I wherein $Ar^1$ is 2-oxoindolin-5-yl, 2,3-dioxoindolin-5-yl, 2-oxo-2,3-dihydrobenzimidazol-5-yl, 2-oxo-2,3-dihydrobenoxazol-5-yl, 2-oxo-2,3-dihydrobenzothiazol-5-yl, 2-oxo-1,2-dihydroquinolin-3-yl, 2-oxo-1,2-dihydroquinolin-6-yl, 2-oxo-1,2-dihydroquinolin-7-yl, 3-oxo-2,3-dihydro-4H-1,4-benzoxazin-7-yl or 3-oxo-2,3-dihydro-4H-1,4-benzothiazol-7-yl, which may optionally bear one, two or three substituents selected from fluoro, chloro, methyl, ethyl, 2-fluoroethyl, phenyl and benzyl;

$A^1$ is a direct link to $X^1$, or is methylene;

$X^1$ is oxy, thio, sulphinyl or sulphonyl;

$Ar^2$ is 1,3-phenylene or 1,4-phenylene which may optionally bear one or two substituents selected from fluoro, chloro, hydroxy, amino, nitro, ureido, methoxy, dimethylamino, trifluoromethyl and acetamido; or $Ar^2$ is 3,5-pyridylene;

$R^1$ is methylthio, ethylthio, propylthio, methylsulphinyl, ethylsulphinyl, propylsulphinyl, methylsulphonyl, ethylsulphonyl, propylsulphonyl, methylamino, ethylamino, dimethylamino or diethylamino, or $R^1$ is cyano, carbamoyl, methoxycarbonyl, ethoxycarbonyl, propoxycarbonyl, N-methylcarbamoyl, N-ethylcarbamoyl, N,N-dimethylcarbamoyl, N,N-diethylcarbamoyl, hydroxymethyl, 2-hydroxyethyl, 3-hydroxypropyl, methoxymethyl, ethoxymethyl, 2-methoxyethyl, 2-ethoxyethyl, 3-methoxypropyl or 3-ethoxypropyl; and $R^2$ and $R^3$ together form a group of the formula —$A^2$—$X^2$—$A^3$— which, together with the carbon atom to which $A^2$ and $A^3$ are attached, defines a ring having 5 or 6 ring atoms, wherein $A^2$ is ethylene, $A^3$ is methylene or ethylene, and $X^2$ is oxy, and which ring may bear one or two substituents selected from methyl and ethyl;

or a pharmaceutically-acceptable salt thereof.

A further preferred compound of the invention comprises a cyclic ether derivative of the formula I wherein $Ar^1$ is naphth-2-yl which may optionally bear one or two substituents selected from fluoro, chloro, methyl, methoxy and trifluoromethyl, or $Ar^1$ is 2-oxo-1,2-dihydroquinolin-6-yl which may optionally bear one or two substituents selected from fluoro, chloro, methyl and ethyl;

$A^1$ is a direct link to $X^1$, or is methylene;

$X^1$ is oxy, thio, sulphinyl or sulphonyl;

$Ar^2$ is 1,3-phenylene which may optionally bear a substituent selected from fluoro, chloro and trifluoromethyl;

$R^1$ is methylthio, ethylthio, propylthio, isopropylthio, tert-butylthio, methylsulphinyl, ethylsulphinyl, propylsulphinyl, hydrogen, formyl, cyano, methoxycarbonyl, ethoxycarbonyl, propoxycarbonyl, hydroxymethyl, 1-hydroxyethyl, 2-hydroxyethyl, 2,2,2-trifluoroethylthio, acetyl, propionyl, methoxymethyl, ethoxymethyl or 2-methoxyethyl; and $R^2$ and $R^3$ together form a group of the formula —$A^2$—$X^2$—$A^3$— which, together with the carbon atom to which each of $A^2$ and $A^3$ is attached, defines a ring having 5 or 6 ring atoms, and $X^2$ is oxy, and which ring may bear one or two substituents selected from methyl and ethyl; or a pharmaceutically-acceptable salt thereof.

A further preferred compound of the invention comprises a cyclic ether derivative of the formula I wherein $Ar^1$ is phenyl which may optionally bear a substituent selected from fluoro, chloro, methyl, tert-butyl, phenyl and benzoyl, and wherein said phenyl or benzoyl substituent may optionally bear a chloro substituent, or $Ar^1$ is naphth-2-yl which may optionally bear a substituent selected from fluoro, chloro and methyl;

$A^1$ is a direct link to $X^1$, or is methylene;

$X^1$ is oxy, thio, sulphinyl or sulphonyl;

$Ar^2$ is 1,3-phenylene which may optionally bear one or two substituents selected from fluoro and trifluoromethyl;

$R^1$ is methylthio, ethylthio, methylsulphinyl, ethylsulphinyl, methylsulphonyl or ethylsulphonyl; and $R^2$ and $R^3$ together form a group of the formula —$A^2$—$X^2$—$A^3$— which, together with the carbon atom to which $A^2$ and $A^3$ is attached, defines a ring having 5 or 6 ring atoms, wherein $A^2$ is ethylene, $A^3$ is methylene or ethylene and $X^2$ is oxy, and which ring may bear a substituent selected from methyl and ethyl;

or a pharmaceutically-acceptable salt thereof.

A further preferred compound of the invention comprises a cyclic ether derivative of the formula I wherein $Ar^1$ is phenyl which may optionally bear a substituent selected from fluoro, chloro, methyl, tert-butyl, phenyl and benzoyl, and wherein said phenyl or benzoyl substituent may optionally bear a chloro substituent, or $Ar^1$ is naphth-2-yl which may optionally bear a substituent selected from fluoro, chloro and methyl;

$A^1$ is a direct link to $X^1$ or is methylene;

$X^1$ is oxy, thio, sulphinyl or sulphonyl;

$Ar^2$ is 1,3-phenylene which may optionally bear one or two substituents selected from fluoro and trifluoromethyl;

$R^1$ is cyano, methoxycarbonyl, ethoxycarbonyl, hydroxymethyl, 2-hydroxyethyl, methoxymethyl, ethoxymethyl, 2-methoxyethyl or 2-ethoxyethyl; and $R^2$ and $R^3$ together form a group of the formula —$A^2$—$X^2$—$A^3$— which, together with the carbon atom to which $A^2$ and $A^3$ is attached, defines a ring having 5 or 6 ring atoms, wherein $A^2$ is ethylene, $A^3$ is methylene or ethylene and $X^2$ is oxy, and which ring may bear a substituent selected from methyl and ethyl;

or a pharmaceutically-acceptable salt thereof.

A further preferred compound of the invention comprises a cyclic ether derivative of the formula I wherein $Ar^1$ is 1,3-dimethyl-2-oxo-2,3-dihydrobenzimidazol-5-yl, 3-methyl-2-oxo-2,3-dihydrobenzothiazol-6-yl, 1-methyl-2-oxo-1,2-dihydroquinolin-6-yl, 1-ethyl-2-oxo-1,2-dihydroquinolin-6-yl, 4-methyl-3-oxo-2,3-dihydro-4H-1,4-benzoxazin-7-yl or 2,2,4-trimethyl-3-oxo-2,3-dihydro-4H-1,4-benzoxazin-7-yl;

$A^1$ is a direct link to $X^1$, or is methylene;

$X^1$ is oxy, thio, sulphinyl or sulphonyl;

$Ar^2$ is 1,3-phenylene which may optionally bear one or two substituents selected from fluoro and trifluoromethyl;

$R^1$ is methylthio, ethylthio, methylsulphinyl, ethylsulphinyl, methylsulphonyl or ethylsulphonyl; and $R^2$ and $R^3$ together form a group of the formula —$A^2$—$X^2$—$A^3$— which, together with the carbon atom to which $A^2$ and $A^3$ is attached, defines a ring atom having 5 or 6 ring atoms, wherein $A^2$ is ethylene, $A^3$ is methylene or ethylene and $X^2$ is oxy, and which ring may bear a substituent selected from methyl and ethyl;

or a pharmaceutically-acceptable salt thereof.

A further preferred compound of the invention comprises a cyclic ether derivative of the formula I wherein $Ar^1$ is 1,3-dimethyl-2-oxo-2,3-dihydrobenzimidazol-5-yl, 3-methyl-2-oxo-2,3-dihydrobenzothiazol-6-yl, 1-methyl-2-oxo-1,2-dihydroquinolin-6-yl, 1-ethyl-2-oxo-1,2-dihydroquinolin-6-yl, 4-methyl-3-oxo-2,3-dihydro-4H-1,4-benzoxazin-7-yl or 2,2,4-trimethyl-3-oxo-2,3-dihydro-4H-1,4-benzoxazin-7-yl;

$A^1$ is a direct link to $X^1$, or is methylene;

$X^1$ is oxy, thio, sulphinyl or sulphonyl;

$Ar^2$ is 1,3-phenylene which may optionally bear one or two substituents selected from fluoro and trifluoromethyl;

$R^1$ is cyano, methoxycarbonyl, ethoxycarbonyl, hydroxymethyl or methoxymethyl; and $R^2$ and $R^3$ together form a group of the formula —$A^2$—$X^2$—$A^3$— which, together with the carbon atom to which $A^2$ and $A^3$ is attached, defines a ring having 5 or 6 ring atoms, wherein $A^3$ is ethylene, is methylene or ethylene and $X^2$ is oxy, and which ring may bear a substituent selected from methyl and ethyl;

or a pharmaceutically-acceptable salt thereof.

A further preferred compound of the invention comprises a cyclic ether derivative of the formula I wherein $Ar^1$ is naphth-2-yl which may optionally bear a fluoro substituent, or $Ar^1$ is 1-methyl-2-oxo-1,2-dihydroquinolin-6-yl;

$A^1$ is methylene and $X^1$ is oxy;

$Ar^2$ is 1,3-phenylene or 5-fluoro-1,3-phenylene;

$R^1$ is methylthio, ethylthio, isopropylthio, tert-butylthio, methylsulphinyl, hydrogen, formyl, cyano, methyl, ethyl, ethoxycarbonyl, hydroxymethyl, 1-hydroxyethyl, 2,2,2-trifluoroethylthio, acetyl or methoxymethyl; and $R^2$ and $R^3$ together form a group of the formula —$A^2$—$X^2$—$A^3$— which, together with the carbon atom to which each of $A^2$ and $A^3$ is attached, defines a ring having 6 ring atoms, wherein $A^2$ is ethylene, $A^3$ is ethylene and $X^2$ is oxy, and which ring may bear a methyl substituent alpha to $X^2$;

or a pharmaceutically-acceptable salt thereof.

Specific especially preferred compounds of the invention include the following cyclic ether derivatives of the formula I, or pharmaceutically-acceptable salts thereof:

4-methylthio-4-[3-(naphth-2-ylmethoxy)phenyl]tetrahydropyran and
4-ethoxycarbonyl-4-[3-(1-methyl-2-oxo-1,2-dihydroquinolin-6-ylmethoxy)phenyl]tetrahydropyran.

Further specific especially preferred compounds of the invention include the following cyclic ether derivatives of the formula I, or pharmaceutically-acceptable salts thereof:

4-acetyl-4-[3-(1-methyl-2-oxo-1,2-dihydroquinolin-6-ylmethoxy)phenyl]tetrahydropyran,
4-[5-fluoro-3-(1-methyl-2-oxo-1,2-dihydroquinolin-6-ylmethoxy)phenyl]-3,4,5,6-tetrahydro-2H-pyran,
4-ethyl-4-13-(1-methyl-2-oxo-1,2-dihydroquinolin-6-ylmethoxy)phenyl]tetrahydropyran,
(2RS,4RS)-4-ethyl-4-[5-fluoro-3-(1-methyl-2-oxo-1,2-dihydroquinolin-6-ylmethoxy)phenyl]-2-methyl-tetrahydropyran and
4-[5-fluoro-3-(1-methyl-2-oxo-1,2-dihydroquinolin-6-ylmethoxy)phenyl]-4-methylthiotetrahydropyran.

A compound of the invention comprising a cyclic ether derivative of the formula I, or a pharmaceutically-acceptable salt thereof, may be prepared by any process known to be applicable to the preparation of structurally-related compounds. Such procedures are provided as a further feature of the invention and are illustrated by the following representative examples in which, unless otherwise stated, $Ar^1$, $A^1$, $X^1$, $Ar^2$, $R^1$, $R^2$ and $R^3$ have any of the meanings defined hereinbefore.

(a) The coupling, preferably in the presence of a suitable base, of a compound of the formula $Ar^1$—$A^1$—$X^1$—H with a compound of the formula II wherein Z is a displaceable group; provided that, when there is an amino, alkylamino or hydroxy group in $Ar^1$, $Ar^2$, $R^1$, $R^2$ or $R^3$, any amino alkylamino or hydroxy group may be protected by a conventional protecting group or alternatively any such group need not be protected, whereafter any undesired protecting group in $Ar^1$, $Ar^2$, $R^1$, $R^2$, $R^3$ is removed by conventional means.

A suitable displaceable group Z is, for example, a halogeno or sulphonyloxy group, for example a chloro, bromo, iodo, methanesulphonyloxy or toluene-p-sulphonyloxy group.

A suitable base for the coupling reaction is, for example, an alkali or alkaline earth metal carbonate, (1-4C)alkoxide, hydroxide or hydride, for example sodium carbonate, potassium carbonate, sodium ethoxide, sodium butoxide, sodium hydroxide, potassium hydroxide, sodium hydride or potassium hydride. The coupling reaction is conveniently performed in a suitable inert solvent or diluent, for example N,N-dimethylformamide, N,N-dimethylacetamide, N-methylpyrrolidin-2-one, dimethylsulphoxide, acetone, 1,2-dimethoxyethane or tetrahydrofuran, and at a temperature in the range, for example, 10° to 150° C., conveniently at or near 100° C.

Conveniently the reaction may be performed in the presence of a suitable catalyst, for example a metallic catalyst, for example palladium(O) or copper(I) such as tetrakis(triphenylphosphine)palladium, cuprous chloride or cuprous bromide.

A suitable protecting group for an amino or alkylamino group is, for example, an acyl group for example a (2-4C)alkanoyl group (especially acetyl), a (1-4C)alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl or alkoxycarbonyl or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-charcoal.

A suitable protecting group for a hydroxy group is, for example, an acyl group, for example a (2-4C)alkanoyl group (especially acetyl), an aroyl group (especially benzoyl) or an arylmethyl group (especially benzyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-charcoal.

The starting materials of the formula $Ar^1$—$A^1$—$X^1$—H and of the formula II may be obtained by standard procedures of organic chemistry.

(b) The coupling, preferably in the presence of a suitable base as defined hereinbefore, of a compound of the formula III with a compound of the formula $Ar^1$—$A^1$—Z wherein Z is a displaceable group as defined hereinbefore; provided that, when there is an amino, alkylamino or hydroxy group in $Ar^1$, $Ar^2$, $R^1$, $R^2$ or $R^3$, any amino, alkylamino or hydroxy group may be protected by a conventional protecting group as defined hereinbefore or alternatively any such group need not be protected, whereafter any undesired protecting group in $Ar^1$, $Ar^2$, $R^1$, $R^2$ or $R^3$ is removed by conventional means.

The coupling reaction is conveniently performed in a suitable inert solvent as defined hereinbefore and at a temperature in the range, for example, 10° to 150° C., conveniently at or near 100° C. The reaction may conveniently be performed in the presence of a suitable catalyst as defined hereinbefore.

The starting materials of the formula $Ar^1$—$A^1$—Z and of the formula III may be obtained by standard procedures of organic chemistry. The preparation of such starting materials is described within the accompanying non-limiting Examples which are provided for the purpose of illustration only. Other necessary starting materials are obtainable by analogous procedures to those described or by modifications thereto which are within the ordinary skill of an organic chemist.

(c) For the production of those compounds of the formula I wherein $R^1$ is (1-4C)alkylthio, the alkylation, preferably in the presence of a suitable base as defined hereinbefore, of a compound of the formula IV with a compound of the formula $R^4$—Z, wherein Z has the meaning defined hereinbefore and $R^4$ is a (1-4C)alkyl group; provided that, when there is an amino, imino, alkylamino or hydroxy group in $Ar^1$, $Ar^2$, $X^1$, $R^2$ or $R^3$ any amino, imino, alkylamino or hydroxy group may be protected by a conventional protecting group or alternatively any such group need not be protected, whereafter any undesired protecting group in $Ar^1$, $Ar^2$, $X^1$, $R^2$ or $R^3$ is removed by conventional means.

A suitable protecting group for an imino group is, for example, any of the protecting groups defined hereinbefore for an amino or alkylamino group.

The starting material of the formula IV may be obtained by standard procedures of organic chemistry. The preparation of such starting materials is described within the accompanying non-limiting Examples which are provided for the purpose of illustration only.

(d) For the production of those compounds of the formula I wherein $X^1$ is a sulphinyl or sulphonyl group, wherein $R^1$ is a (1-4C)alkylsulphinyl or (1-4C)alkylsulphonyl group, or wherein $R^2$ and $R^3$ together form a group of the formula —$A^2$—$X^2$—$A^3$— and $X^2$ is a sulphinyl or sulphonyl group, the oxidation of a compound of the formula I wherein $X^1$ is a thio group, wherein $R^1$ is a (1-4C)alkylthio group, or wherein $R^2$ and $R^3$ together form a group of the formula —$A^2$—$X^2$—$A^3$— and $X^2$ is a thio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

(e) For the production of those compounds of the formula I wherein $Ar^2$ bears an alkanoylamino substituent, the acylation of a compound of the formula I wherein $Ar^2$ bears an amino substituent.

A suitable acylating agent is, for example, any agent known in the art for the acylation of amino to acylamino, for example an acyl halide, for example a (2-6C)alkanoyl chloride or bromide, in the presence of a suitable base, an alkanoic acid anhydride, for example a (2-6C)alkanoic acid anhydride, or an alkanoic acid mixed anhdride, for example the mixed anhydride formed by the reaction of an alkanoic acid and a (1-4C)alkoxycarbonyl halide, for example a (1-4C)alkoxycarbonyl chloride, in the presence of a suitable base. In general the reaction is carried out in a suitable solvent or diluent such as methylene chloride, acetone, tetrahydrofuran or tert-butyl methyl ether and at a temperature, for example, at or near ambient temperature, that is in the range 15° to 35° C. A suitable base when it is required is, for example, pyridine, 4-dimethylaminopyridine, triethylamine, ethyldiisopropylamine, N-methylmorpholine, an alkali metal carbonate, for example potassium carbonate, or an alkali metal carboxylate, for example sodium acetate.

(f) For the production of those compounds of the formula I wherein $Ar^1$ bears an alkyl or substituted alkyl substituent on an available nitrogen atom, wherein $Ar^2$ bears an alkoxy substituent or wherein $R^1$ is an alkoxyalkyl group, the alkylation of a compound of the formula I wherein $Ar^1$ bears a hydrogen atom on said available nitrogen atom, wherein $Ar^2$ bears a hydroxy substituent or wherein $R^1$ is a hydroxyalkyl group.

A suitable alkylating agent is, for example, any agent known in the art for the alkylation of an available nitrogen atom, or of hydroxy to alkoxy, for example an alkyl or substituted alkyl halide, for example a (1-6C)alkyl chloride, bromide or iodide or a substituted (1-4C)alkyl chloride, bromide or iodide, in the presence of a suitable base. A suitable base for the alkylation reaction is, for example, an alkali or alkaline earth metal carbonate, sodium hydroxide, potassium hydroxide, sodium hydride or potassium hydride. The alkylation reaction is preferably performed in a suitable inert solvent or diluent, for example N,N-dimethylformamide, dimethylsulphoxide, acetone, 1,2-dimethoxyethane or tetrahydrofuran, and at a temperature in the range, for example, 10° to 150° C., conveniently at or near ambient temperature.

When a pharmaceutically-acceptable salt of a novel compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

Many of the intermediates defined herein are novel, for example those of the formula IV and this is provided as a further feature of the invention.

As stated previously, the novel compounds of the formula I are inhibitors of the enzyme 5-LO. The effects of this inhibition may be demonstrated using one or more of the standard procedures set out below:

a) An in vitro spectrophotometric enzyme assay system, which assesses the inhibitory properties of a test compound in a cell free system using 5-LO isolated from guinea pig neutrophils and as described by D. Aharony and R. L. Stein (*J. Biol. Chem.*, 1986, 261(25), 11512–11519). This test provides a measure of the intrinsic inhibitory properties of a test compound against soluble 5-LO in an extracellular environment.

b) An in vitro assay system involving incubating a test compound with heparinised human blood, prior to challenge with the calcium ionophore A23187 and then indirectly measuring the inhibitory effects on 5-LO by assaying the amount of $LTB_4$ using specific radioimmunoassays described by Carey and Forder (F. Carey and R. A. Forder, *Prostaglandins, Leukotrienes Med.*, 1986, 22, 57; *Prostaglandins*, 1984, 28, 666; *Brit. J. Pharmacol.* 1985, 84, 34P) which involve the use of a protein-$LTB_4$ conjugate produced using the procedure of Young et alia (*Prostaglandins*, 1983, 26(4), 605–613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane $B_2(TxB_2)$ described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

c) An ex vivo assay system, which is a variation of test b) above, involving administration of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $TxB_2$. This test provides an indication of the bioavailability of a test compound as an inhibitor of 5-LO or cyclooxygenase.

d) An in vitro assay system involving the measurement of the inhibitory properties of a test compound against the liberation of $LTC_4$ and $PGE_2$ induced by zymosan on mouse resident peritoneal macrophages, using the procedure of Humes (J. L. Humes et alia, *Biochem. Pharmacol.*, 1983, 32, 2319–2322) and conventional radioimmunoassay systems to measure $LTC_4$ and $PGE_2$. This test provides an indication of inhibitory effects against 5-LO and cyclooxygenase in a non-proteinaceous system.

e) An in vivo system involving the measurement of the effects of a test compound in inhibiting the inflammatory response to arachidonic acid in the rabbit skin model developed by D. Aked et alia (*Brit. J. Pharmacol.*, 1986, 89, 431–438). This test provides an in vivo model for 5-LO inhibitors administered topically or orally.

f) An in vivo system involving measuring the effects of a test compound administered orally or intravenously on a leukotriene dependent bronchoconstriction induced by an antigen challenge in guinea pigs pre-dosed with an antihistamine (mepyramine), a β-adrenergic blocking agent (propranolol), and a cyclooxygenase inhibitor (indomethacin), using the procedure of W. H. Anderson et alia (*British J. Pharmacology*, 1983, 78(1), 67–574). This test provides a further in vivo test for detecting 5-LO inhibitors.

g) An in vivo system involving measuring the effects of a test compound administered orally against the liberation of $LTB_4$ induced by zymosan within an air pouch generated within the subcutaneous tissue of the back of male rats. The rats are anaesthetised and air pouches are formed by the injection of sterile air (20 ml). A further injection of air (10 ml) is similarly given after 3 days. At 6 days after the initial air injection the test compound is administered (usually orally as the suspension produced when a solution of the test compound in dimethylsulphoxide is added to hydroxypropylmethylcellulose), followed by the intrapouch injection of zymosan (1 ml of a 1% suspension in physiological saline). After 3 hours the rats are killed, the air pouches are lavaged with physiological saline, and the specific radioimmunoassay described above is used to assay $LTB_4$ in the washings. This test provides an indication of inhibitory effects against 5-LO in an inflammatory milieu.

Although the pharmacological properties of the compounds of the formula I vary with structural changes as expected, in general compounds of the formula I possess 5-LO inhibitory effects at the following concentrations or doses in one or more of the above tests a)–f):

Test a): $IC_{50}$ in the range, for example, 0.01–30 μM;

Test b): $IC_{50}$ ($LTB_4$) in the range, for example, 0.01–40 μM $IC_{50}$ ($TxB_2$) in the range, for example, 40–200 μM;

Test c): oral $ED_{50}(LTB_4)$ in the range, for example, 1–100 mg/kg;

Test d): $IC_{50}$ ($LTC_4$) in the range, for example, 0.001–1 μM, $IC_{50}$ ($PGE_2$) in the range, for example, 20–1000 μM;

Test e): inhibition of inflammation in the range, for example, 0.3–100 μg intradermally;

Test f): $ED_{50}$ in the range, for example, 0.5–1 0mg/kg i.v.;

Test g): oral $ED_{50}(LTB_4)$ in the range, for example, 0.5–50 mg/kg.

No overt toxicity or other untoward effects are present in tests c), e), f) and/or g) when compounds of the formula I are administered at several multiples of their minimum inhibitory dose or concentration.

Thus, by way of example, the compound 4-methylthio-4-[3-(naphth-2-ylmethoxy)phenyl]tetrahydropyran has an $IC_{50}$ of 0.05 μM against $LTB_4$ in test b), and an oral $ED_{50}$ of 8 mg/kg versus $LTB_4$ in test g); and the compound 4-ethoxycarbonyl-4-[3-(1-methyl-2-oxo-1,2-dihydroquinolin-6-ylmethoxy)tetrahydropyran has an $IC_{50}$ of 0.05 μM aganst $LTB_4$ in test b). In general those compounds of the formula I which are particularly preferred have an $IC_{50}$ of <1 μM against $LTB_4$ in test b), and an oral $ED_{50}$ of <100 mg/kg against $LTB_4$ in tests c) and/or g).

These compounds are examples of compounds of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises a cyclic ether derivative of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is a cyclic ether derivative of the formula I, or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a cyclic ether derivative of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a compound of the formula I will naturally vary according to the nature and severity of the conditions, the age and sex of the animal or patient and the route of administration, according to well known principles of medicine. As mentioned above, compounds of the formula I are useful in treating those allergic and inflammatory conditions which are due alone or in part to the effects of the metabolites of arachidonic acid arising by the linear (5-LO catalysed) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovascular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicylic acid, ibuprofen, sulindac, rolmerin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises a cyclic ether derivative of the formula I, or a pharmaceutically-acceptable salt thereof as defined hereinbefore, in conjunction or admixture with a cyclooxygenase inhibitory non-steroidal anti-inflammatory agent (such as mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The invention will now be illustrated in the following non-limiting Examples in which, unless otherwise stated:
(i) evaporations were carried out by rotary evaporation in vacuo and work-up procedures were carried out after removal of residual solids by filtration;
(ii) operations were carried out at room temperature, that is in the range 18°–25° and under an atmosphere of an inert gas such as argon;
(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Meck, Darmstadt, W. Germany;
(iv) yields are given for illustration only and are not necessarily the maximum attainable;
(v) the end-products of the formula I have satisfactory microanalyses and their structures were confirmed by NMR and mass spectral techniques;
(vi) intermediates were not generally fully characterised and purity was assessed by thin layer chromatographic, infra-red (IR) or NMR analysis;
(vii) melting points are uncorrected and were determined using a Merrier SP62 automatic melting point apparatus or an oil-bath apparatus; melting points for the end-products of the formula I were determined after recrystallisation from a conventional organic solvent such as ethanol, methanol, acetone, ether or hexane, alone or in admixture; and
(viii) the following abbreviations have been used:
THF tetrahydrofuran;
DMSO dimethylsulphoxide;
DMF N,N-dimethylformamide;
DMA N,N-dimethylacetamide.

EXAMPLE 1

Sodium hydride (50% w/w dispersion in mineral oil, 0.05 g) was added to a solution of 4-mercapto-4-[3-(naphth-2-ylmethoxy)phenyl]tetrahydropyran (0.32 g) in DMF (3 ml) and the mixture was stirred at ambient temperature for 30 minutes. Methyl iodide (0.2 ml) was added and the mixture was stirred at ambient temperature for 1 hour. The mixture was poured onto water (10 ml) and neutralised by the addition of dilute aqueous hydrochloric acid. The mixture was extracted with diethyl ether. The organic extract was washed with water, dried ($MgSO_4$) and evaporated. The residue was purified by column chromatography using a 9:1 v/v mixture of hexane and ethyl acetate as eluent. There was thus obtained 4-methylthio-4-[3-(naphth-2-ylmethoxy)phenyl]tetrahydropyran (0.217 g, 65%), m.p. 95°–97° C.

The 4-mercapto-4-[3-(naphth-2-ylmethoxy)phenyl]-tetrahydropyran used as a starting material was obtained as follows:

A Grignard reagent was prepared by heating a mixture of 3-(naphth-2-ylmethoxy)bromobenzene (3 g), magnesium powder (0.23 g) and THF (12 ml) to 30° C. for 1.5 hours. The reagent was cooled to 20° C. and a solution of tetrahydropyran-4-one (0.88 ml) in THF (5 ml) was added dropwise. The mixture was heated to 30° C. for 15 hours, evaporated and the residue was partitioned between ethyl acetate and water. The organic layer was separated, washed with brine, dried ($MgSO_4$) and evaporated. The residue was purified by column chromatography using a 7:3 v/v mixture of methylene chloride and diethyl ether as eluent. There was thus obtained 4-hydroxy-4-[3-(naphth-2-ylmethoxy)phenyl]-tetrahydropyran (2.06 g, 42%), m.p. 130°–131° C.

A mixture of a portion (1.67 g) of the product so obtained, Lawesson's reagent [2,4-bis-(4-methoxyphenyl)-1,3-dithia-2,4-diphosphetane-2,4-disulphide; 1.10 g] and methylene chloride (30 ml) was stirred at ambient temperature for 1.5 hours. The mixture was evaporated and the residue was partitioned between diethyl ether and water. The organic phase was washed with water and brine, dried ($MgSO_4$) and evaporated.

The residue was purified by column chromatography using a 19:1 v/v mixture of toluene and ethyl acetate as eluent. There was thus obtained the required starting material (0.32 g, 18%), m.p. 106°–109° C.

EXAMPLE 2

A mixture of 6-bromomethyl-1-methyl-1,2-dihydroquinolin-2-one (0.1 g), 4-ethoxycarbonyl-4-(3-hydroxyphenyl)tetrahydropyran (0.098 g), potassium carbonate (0.057 g) and DMF (2 ml) was stirred at ambient temperature for 16 hours. The mixture was partitioned between diethyl ether and 0.5N aqueous hydrochloric acid. The organic layer was washed with water and brine, dried (MgSO$_4$) and evaporated. The residue was purified by column chromatography using initially methylene chloride and then increasingly polar mixtures of methylene chloride and acetone as eluent. There was thus obtained an oil which was triturated in pentane to give 4-ethoxycarbonyl-4-[3-(1-methyl-2-oxo-1,2-dihydroquinolin-6-ylmethoxy)phenyl]tetrahydropyran (0.099 g, 60%), m.p. 109°–110° C.

NMR Spectrum (CDCl$_3$, δ values) 1.15 (t, 3H), 1.8–2.65 (m, 4H), 3.40–4.10 (m, 4H), 3.75 (s, 3H), 4.15 (q, 2H), 5.10 (s, 2H), 6.65–7.80 (m, 9H).

The 6-bromomethyl-1-methyl-1,2-dihydroquinolin-2-one, used as a starting material was obtained as follows:

A mixture of 1,2-dihydro-1,6-dimethylquinolin-2-one (4.4 g; *Helv. Chim. Acta.*, 1970, 53, 1903), N-bromosuccinimide (4.53 g), azobisisobutyronitrile (0.01 g) and carbon tetrachloride (75 ml) was heated to reflux for 3 hours. The mixture was evaporated and the residue was partitioned between ethyl acetate and water. The organic phase was washed with water, dried (MgSO$_4$) and evaporated. The residue was purified by column chromatography using a 2:1 v/v mixture of toluene and ethyl acetate as cluehr. There was thus obtained the required starting material (4.8 g, 75%), as a solid, m.p. 107°–108° C.

NMR Spectrum (CDCl$_3$, δ values) 3.7 (s, 3H), 4.57 (s, 2H), 6.7–7.5 (d, 1H), 7.25–7.65 (m, 4H).

The 4-ethoxycarbonyl-4-(3-hydroxyphenyl)tetrahydropyran used as a starting material was obtained as follows:

A mixture of 3-hydroxyphenylacetic acid (10 g), ethanol (150 ml) and concentrated sulphuric acid (0.5 ml) was stirred at ambient temperature for 16 hours. The mixture was evaporated and the residue was partitioned between methylene chloride and water. The organic phase was washed with water and brine, dried (MgSO$_4$) and evaporated. The residue was purified by column chromatography using initially methylene chloride and then increasingly polar mixtures of methylene chloride and acetone as eluent. There was thus obtained ethyl 3-hydroxyphenylacetate (11.4 g, 96%), IR Spectrum 1690–1740 cm$^-$.

A mixture of the product so obtained, benzyl bromide (10.82 g), potassium carbonate (9.6 g) and DMF (110 ml) was stirred at ambient temperature for 16 hours. The mixture was partitioned between diethyl ether and water. The organic phase was washed with water and brine, dried (MgSO$_4$) and evaporated. The residue was purified by column chromatography using methylene chloride as eluent. There was thus obtained ethyl 3-benzyloxyphenylacetate (13.8 g, 80%), IR Spectrum 1720–1740 cm$^{-1}$.

Sodium hydride (60% w/w dispersion in mineral oil, 0.176 g) was added to a mixture of the ester so obtained (0.54 g), 1,4,7,10,13-pentaoxacyclopentadecane (hereinafter 15-crown-5, 3 drops) and DMF (10 ml) and the mixture was stirred at ambient temperature for 25 minutes. Sodium iodide (0.3 g) and bis-2-chloroethyl ether (0.488 g) were added in turn and the mixture was stirred at ambient temperature for 16 hours. The mixture was partitioned between diethyl ether and 0.5N aqueous hydrochloric acid. The organic phase was washed with water and brine, dried (MgSO$_4$) and evaporated. The residue was purified by column chromatography using initially methylene chloride and then a 19:1 v/v mixture of methylene chloride and diethyl ether as eluent. There was thus obtained 4-(3-benzyloxyphenyl)-4-ethoxycarbonyltetrahydropyran (0.325 g, 48%), m.p. 70°–71° C.

A mixture of a portion (0.3 g) of the product so obtained, 10% palladium-on-charcoal catalyst (0.05 g) and ethanol (8 ml) was stirred under 2 atmospheres of hydrogen for 16 hours. The mixture was filtered and evaporated. The residue was purified by column chromatography using increasingly polar mixtures of methylene chloride and acetone as eluent. There was thus obtained the required starting material (0.2 g, 91%), m.p. 100°–101° C.

EXAMPLE 3

The procedure described in Example 2 was repeated except that 2-bromomethyl-7-fluoronaphthalene was used in place of 6-bromomethyl-1-methyl-1,2-dihydroquinolin-2-one. There was thus obtained 4-ethoxycarbonyl-4-[3-(7-fluoronaphth-2-ylmethoxy)phenyl]tetrahydropyran in 76% yield, m.p. 91°–92° C.

Elemental Analysis: Found C, 73.0; H, 6.2; C$_{25}$H$_{25}$FO$_4$ requires C, 73.5; H, 6.1%.

The 2-bromomethyl-7-fluoronaphthalene used as a starting material was obtained as follows:

3-Fluorobenzyl chloride was reacted with acetylacetaldehyde dimethyl acetal using the procedure described for the corresponding reaction of 3-methylbenzyl chloride (*Synthesis*, 1974, 566). There was thus obtained 4-(3-fluorophenyl)-3-hydroxy-3-methylbutanal dimethyl acetal (b.p. 125°–135° C. at 0.25 mm Hg). A mixture of the material so obtained (15 g), glacial acetic acid (60 ml) and hydrobromic acid (48% w/v. 48 ml) was heated on a steam bath for 1 hour. The mixture was evaporated and the residue was purified by column chromatography using petroleum ether (b.p. 60°–80° C.) as eluent. There was thus obtained 7-fluoro-2-methylnaphthalene (4 g).

A mixture of 7-fluoro-2-methylnaphthalene (3 g), N-bromosuccinimide (3.3 g), 2,2'-azobisisobutyronitrile (0.2 g) and carbon tetrachloride (100 ml) was heated to reflux for 1 hour. The mixture was cooled to ambient temperature and filtered. The filtrate was evaporated and the residue was purified by column chromatography using a 19:1 v/v mixture of petroleum ether (b.p. 60°–80° C.) and toluene as eluent. There was thus obtained 2-bromomethyl-7-fluoronaphthalene (2.8 g), m.p., 62° C.

EXAMPLE 4

Using the procedure described in the third paragraph of the portion of Example 2 which is concerned with the preparation of 4-ethoxycarbonyl-4-(3-hydroxyphenyl])tetrahydropyran, 3-(1-methyl-2-oxo-1,2-dihydroquinolin-6-ylmethoxy)phenylacetonitrile was reacted with bis-2-chloroethyl ether to give 4-cyano-4-[3-(1-methyl-2-oxo-1,2-dihydroquinolin-6-ylmethoxy)-phenyl]tetrahydropyran in 61% yield, m.p. 149°–150°

C. (recrystallised from a mixture of methylene chloride and diethyl ether).

IR Spectrum 2240 cm$^{-1}$.

The 3-(1-methyl-2-oxo-1,2-dihydroquinolin-6-ylmethoxy)phenylacetonitrile used as a starting material was obtained as follows:

The procedure described in Example 2 was repeated except that 3-hydroxyphenylacetonitrile was used in place of 4-ethoxycarbonyl-4-(3-hydroxyphenyl)tetrahydropyran. There was thus obtained the required starting material in 63% yield, m.p. 145°–146° C.

IR Spectrum 2240 cm$^{-1}$.

The 3-hydroxyphenylacetonitrile used above was obtained as follows:

A mixture of m-cresol (10.8 g), tert-butyldimethylsilyl chloride (15 g), imidazole (6.8 g) and DMF (100 ml) was stirred at ambient temperature for 5 hours. The mixture was partitioned between diethyl ether and water. The organic phase was washed with 2N aqueous sodium hydroxide solution and brine, dried (MgSO$_4$) and evaporated. There was thus obtained 3-(tert-butyldimethylsilyloxy)toluene (18.2 g, 82%) as a liquid.

A mixture of the product so obtained (17.2 g), N-bromosuccinimide (16.54 g), 2,2′-azobisisobutyronitrile (1.7 g) and carbon tetrachloride (170 ml) was heated to reflux and irradiated with the light from a 250 Watt lamp for 30 minutes. The mixture was cooled to ambient temperature and filtered. The filtrate was evaporated to give 3-(tert-butyldimethylsilyloxy)benzyl bromide as a liquid which was used directly. Thus the liquid was dissolved in methylene chloride (150 ml) and the solution was cooled to 0° C. Tetrabutylammonium cyanide (24.6 g) was added and the mixture was stirred at 0° C. for 1.5 hours and at ambient temperature for 2.5 hours. The mixture was evaporated and the residue was purified by column chromatography using increasingly polar mixtures of methylene chloride and petroleum ether (b.p. 40°–60° C.) as eluent. There was thus obtained 3-(tert-butyldimethylsilyloxy)phenylacetonitrile (8 g, 42%) as an oil.

Tetrabutylammonium fluoride (1.6M in THF, 15 ml) was added to a solution of the acetonitrile so obtained (4 g) in THF (15 ml) and the mixture was stirred at ambient temperature for 75 minutes. The mixture was evaporated and the residue was partitioned between ethyl acetate and water. The organic phase was washed with water and brine, dried (MgSO$_4$) and evaporated. There was thus obtained 3-hydroxyphenylacetonitrile (1.85 g, 86%).

IR Spectrum 2280 cm$^{-1}$.

EXAMPLE 5

Using the procedure described in the third paragraph of the portion of Example 2 which is concerned with the preparation of 4-ethoxycarbonyl-4-(3-hydroxyphenyl)tetrahydropyran, 3-(7-fluoronaphth-2-ylmethoxy)phenylacetonitrile was reacted with bis-2-chloroethyl ether to give 4-cyano-4-[3-(7-fluoronaphth-2ylmethoxy)phenyl]tetrahydropyran in 39% yield, m.p. 106°–107° C.

IR Spectrum 2215 cm$^{-1}$.

The 3-(7-fluoronaphth-2-ylmethoxy)phenylacetonitrile used as a starting material was obtained as follows:

Using the procedure described in Example 2, 2-bromomethyl-7-fluoronaphthalene was reacted with 3-hydroxyphenylacetonitrile to give the required starting material in 70% yield, m.p. 86°–87° C.

IR Spectrum 2240 cm$^{-1}$.

EXAMPLE 6

The procedure described in Example 2 was repeated except that 4-hydroxymethyl-4-(3-hydroxyphenyl)tetrahydropyran was used in place of 4-ethoxycarbonyl-4-(3-hydroxyphenyl)tetrahydropyran. There was thus obtained 4-hydroxymethyl-4-[3-(1-methyl-2-oxo-1,2-dihydroquinolin-6-ylmethoxy)phenyl]tetrahydropyran in 71% yield, m.p. 61° C.

The 4-hydroxymethyl-4-(3-hydroxyphenyl)tetrahydropyran used as a starting material was obtained as follows:

A solution of ethyl 3-benzyloxyphenylacetate (0.45 g) in diethyl ether (2 ml) was added to a stirred suspension of lithium aluminium hydride (0.17 g) in diethyl ether (15 ml) and the mixture was stirred at ambient temperature for 10 minutes. Water (10 ml) was cautiously added dropwise to destroy the excess of reducing agent. The mixture was extracted with diethyl ether. The organic phase was dried (MgSO$_4$) and evaporated. There was thus obtained 4-(3-benzyloxyphenyl)-4-hydroxymethyltetrahydropyran (0.375 g) as an oil.

A mixture of the product so obtained, 10% palladium-on-charcoal catalyst (0.04 g) and ethanol (5 ml) was stirred under two atmospheres of hydrogen for 8 hours. The mixture was filtered and the filtrate was evaporated. The residue was purified by column chromatography using increasingly polar mixtures of methylene chloride and acetone as eluent. There was thus obtained the required starting material (0.212 g, 80%), m.p. 115° C.

EXAMPLE 7

Sodium hydride (60% w/w dispersion in mineral oil, 0.017 g) was added to a mixture of 4-hydroxymethyl-4-[3-(1-methyl-2-oxo-1,2-dihydroquinolin-6-ylmethoxy)-phenyl]tetrahydropyran (0.1 g), 15-crown-5 (2 drops) and DMF (1.5 ml) and the mixture was stirred at ambient temperature for 10 minutes. Methyl iodide (0.041 ml) was added and the mixture was stirred at ambient temperature for 12 hours. The mixture was partitioned between ethyl acetate and water. The organic phase was washed with brine, dried (MgSO$_4$) and evaporated. The residue was purified by column chromatography using increasingly polar mixtures of methylene chloride and acetone as eluent. There was thus obtained 4-methoxymethyl-4-[3-(1-methyl-2-oxo-1,2-dihydroquinolin-6-ylmethoxy)phenyl]tetrahydropyran (0.072 g, 70%), m.p. 139°–140° C.

EXAMPLE 8

Using a similar procedure to that described in Example 1, 4-mercapto-4-[3-(naphth-2-ylmethoxy)phenyl]tetrahydropyran was reacted with isopropyl iodide to give 4-isopropylthio-4-[3-(naphth-2-ylmethoxy)phenyl]tetrahydropyran in 67% yield, as an oil.

NMR Spectrum (CDCl$_3$, δ values) 0.9(d, 6H), 2.0–2.4(m, 5H), 3.6–4.0(m, 4H), 5.23(s, 2H), 6.85(m, 1H), 7.1(m, 2H), 7.3(m, 1H), 7.5(m, 3H), 7.9(m, 4H).

EXAMPLE 9

Using a similar procedure to that described in Example 1, 4-mercapto-4-[3-(naphth-2-ylmethoxy)phenyl]tetrahydropyran was reacted with 2,2,2-trifluoroethyl iodide to give 4-[3-(naphth-2ylmethoxy)phenyl]-4-(2,2,2-trifluoroethylthio)tetrahydropyran in 61% yield, m.p. 76°–78° C.

EXAMPLE 10

3-Chloroperoxybenzoic acid (60% purity, 0.24 g) was added portionwise to a stirred solution of 4-methylthio-4-[3-(naphth-2-ylmethoxy)phenyl]tetrahydropyran (0.276 g) in chloroform (5 ml) and the mixture was stirred at ambient temperature for 30 minutes. Calcium hydroxide (0.293 g) was added and the mixture was stirred at ambient temperature for 30 minutes. The mixture was filtered and the filtrate was evaporated. The residue was purified by column chromatography using a mixture of dichloromethane and methanol as eluent. There was thus obtained 4-methylsulphinyl-4-[3-(naphth-2-ylmethoxy)phenyl]tetrahydropyran (0.133 g, 50%), as an oil.

NMR Spectrum (CDCl3, δ values) 1.84(s, 3H), 2.05–2.5(m, 4H), 3.4–4.1(m, 4H), 5.24(s, 2H), 7.0–7.9(m, 11H).

EXAMPLE 11

A mixture of 6-bromomethyl-1-methyl-1,2-dihydroquinolin-2-one (0.36 g), 4-(5-fluoro-3-hydroxyphenyl)-4-methylthiotetrahydropyran (0.363 g), potassium carbonate (0.55 g) and acetone (20 ml) was stirred and heated to reflux for 90 minutes. The mixture was concentrated by evaporation of most of the solvent. The residue was partitioned between ethyl acetate and water. The organic phase was washed with water, dried (MgSO4) and evaporated. The residue was purified by column chromatography using a 1:1 v/v mixture of hexane and ethyl acetate as eluent. There was thus obtained 4-[5-fluoro-3-(1-methyl-2-oxo-1,2-dihydroquinolin-6-ylmethoxy)phenyl]-4-methylthiotetrahydropyran (0.37 g, 60%), m.p. 118°–120° C.

The 4-(5-fluoro-3-hydroxyphenyl)-4-methylthiotetrahydropyran, used as a starting material, was obtained as follows:

Sodium hydride (50% w/w dispersion in mineral oil, 12.4 g) was added portionwise to a mixture of benzyl alcohol (26.7 ml) and DMA (500 ml) and the mixture was stirred at ambient temperature for 1 hour. 1-Bromo-3,5-difluorobenzene (50 g) was added carefully to control the rigour of the ensuing exothermic reaction. The mixture was stirred at ambient temperature for 2 hours and the solvent was evaporated. The residue was partitioned between methylene chloride and water and the organic phase was washed with water (4×50 ml), dried (MgSO4) and evaporated. The residue was purified by distillation to give 3-benzyloxy-1-bromo-5-flurobenzene (41.8 g, 57%), as a colourless liquid (b.p. 124°–130° C. at 0.3 mm Hg).

A solution of a portion (9.75 g) of this product in THF (150 ml) was cooled to −75° C. and n-butyl-lithium (1.6M in hexane, 22 ml) was added dropwise. The mixture was stirred at −75° C. for 1 hour and a solution of tetrahydropyran-4-one (3.47 g) in THF (10 ml) was added dropwise. The mixture was stirred at −75° C. for 1 hour and then allowed to warm to 0° C. A saturated aqueous ammonium chloride solution (50 ml) was added and the organic phase was separated, dried (MgSO4) and evaporated. The residue was purified by column chromatography using a 1:1 v/v mixture of toluene and ethyl acetate as eluent. There was thus obtained 4-(3-benzyloxy-5-fluorophenyl)-4-hydroxytetrahydropyran (7.4 g, 71%) as an oil.

Trifluormethanesulphonic acid (0.2 ml) was added dropwise to a solution of 4-(3-benzyloxy-5-fluorophenyl)-4-hydroxytetrahydropyran (1.2 g) in methanethiol (10 ml) and the mixture was stirred at ambient temperature for 10 minutes. Boron trifluoride etherate (5.6 ml) was added and the mixture was stirred at ambient temperature for 1 hour. The mixture was partitioned between water and diethyl ether. The organic phase was washed with water and with a saturated aqueous sodium bicarbonate solution, dried (MgSO4) and evaporated. The residue was purified by column chromatography using a 3:1 v/v mixture of hexane and ethyl acetate as eluent. There was thus obtained the required starting material (0.83 g, 86%), m.p. 120°–123° C.

EXAMPLE 12

Using a similar procedure to that described in Example 11, 6-bromomethyl-1-methyl-1,2-dihydroquinolin-2-one was reacted with 4-ethylthio-4-(5-fluoro-3-hydroxyphenyl)tetrahydropyran to give 4-ethylthio-4-[5-fluoro-3-(1-methyl-2-oxo-1,2-dihydroquinolin-6-ylmethoxy)phenyl]tetrahydropyran in 40% yield, m.p. 73°–75° C.

The 4-ethylthio-4-(5-fluoro-3-hydroxyphenyl)tetrahydropyran, used as a starting material, was obtained by repetition of the procedure described in the last paragraph of the portion of Example 11 which is concerned with the preparation of starting materials except that ethanethiol was used in place of methanethiol. There was thus obtained the required starting material in 90% yield, m.p. 68°–72° C.

EXAMPLE 13

Using a similar procedure to that described in Example 11, 6-bromomethyl-1-methyl-1,2-dihydroquinolin-2-one was reacted with 4-tert-butylthio-4-(5-fluoro-3-hydroxyphenyl)tetrahydropyran to give 4-tert-butylthio-4-[5-fluoro-3-(1-methyl-2-oxo-1,2-dihydroquinolin-6-ylmethoxy)phenyl]tetrahydropyran in 30% yield, m.p. 54°–56° C.

The 4-tert-butylthio-4-(5-fluoro-3-hydroxyphenyl)tetrahydropyran, used as a starting material, was obtained by repetition of the procedure described in the last paragraph of the portion o[Example 11 which is concerned with the preparation of starting materials except that tert-butanethiol was used in place of methanethiol. There was thus obtained the required starting material in 13% yield, as an oil.

NMR Spectrum (CDCl3, δ values) 1.05(s, 9H), 2.2(t, 4H), 3.6–4.1(m, 4H), 6.5(m, 1H), 6.9(m, 2H).

EXAMPLE 14

A mixture of 6-bromomethyl-1-methyl-1,2-dihydroquinolin-2-one (0.34 g), 4-(1-hydroxyethyl)-4-(3-hydroxyphenyl)tetrahydropyran (0.3 g), potassium carbonate (0.205 g) and DMF (3 ml) was stirred at ambient temperature for 16 hours. The mixture was partitioned between ethyl acetate and water. The organic phase was washed with water and with brine, dried (MgSO4) and evaporated. The residue was purified by column chromatography using ethyl acetate as eluent. There was thus obtained an oil which crystallised upon trituration in a mixture of pentane and diethyl ether. There was thus obtained 4-(1-hydroxyethyl)-4-[3-(1-methyl-2-oxo-1,2-dihydroquinolin-6-ylmethoxy)phenyl]tetrahydropyran (0.366 g, 69%), m.p. 59°–60° C.

The 4-(1-hydroxyethyl)-4-(3-hydroxyphenyl)tetrahydropyran, used as a starting material, was obtained as follows:

A solution of oxalyl chloride (1.463 ml) in methylene chloride (5 ml) was added dropwise to a stirred mixture of DMSO (2.38 ml) and methylene chloride (5 ml) which had been cooled to −70° C. The mixture was stirred at −65° C. for 15 minutes. A solution of 4-(3-benzyloxyphenyl)-4-hydroxymethyltetrahydropyran (5 g) in methylene chloride (5 ml) was added dropwise to the mixture which was maintained at a temperature of −60° C. The mixture was stirred at −60° C. for 1 hour. Triethylamine (11.7 ml) was added and the mixture was stirred at −60° C. for 1.5 hours. The mixture was allowed to warm to ambient temperature and stirred for a further 1.5 hours. The mixture was partitioned between methylene chloride and water. The organic phase was washed with water and with brine, dried (MgSO$_4$) and evaporated. The residue was purified by column chromatography using methylene chloride as eluent. There was thus obtained 4-(3-benzyloxyphenyl)-4-formyltetrahydropyran (3.57 g, 72%) as a solid.

Methylmagnesium bromide (3M in diethyl ether, 2 ml) was added dropwise to a solution of a portion (1.184 g) of the 4-formyltetrahydropyran so obtained in THF (20 ml) and the mixture was stirred at ambient temperature for 16 hours. The mixture was evaporated and the residue was partitioned between methylene chloride and a saturated aqueous ammonium chloride solution. The organic phase was washed with water and with brine, dried (MgSO$_4$) and evaporated. The residue was purified by column chromatography using initially methylene chloride and then a 5:1 v/v mixture of methylene chloride and diethyl ether as eluent. There was thus obtained 4-(3-benzyloxyphenyl)-4-(1-hydroxyethyl)tetrahydropyran (0.96 g, 77%), m.p. 119° C.

A mixture of a portion (0.8 g) of the product so obtained, 10% palladium-on-charcoal catalyst (0.25 g), ethyl acetate (5 ml) and ethanol (10 ml) was stirred under four atmospheres of pressure of hydrogen for 16 hours. The mixture of filtered and the filtrate was evaporated. The residue was purified by column chromatography using initially methylene chloride and then a 4:1 v/v mixture of methylene chloride and acetone as eluent. There was thus obtained 4-(1-hydroxyethyl)-4-(3-hydroxyphenyl)tetrahydropyran (0.472 g, 78%), m.p. 113° C.

EXAMPLE 15

Using a similar procedure to that described in Example 14, 6-bromomethyl-1-methyl-1,2-dihydroquinolin-2-one was reacted with 4-formyl-4-(3-hydroxyphenyl)-tetrahydropyran to give 4-formyl-4-[3-(1-methyl-2-oxo-1,2-dihydroquinolin-6-ylmethoxy)phenyl]tetrahydropyran in 45% yield as a glassy solid.

NMR Spectrum (CDCl$_3$, δ values) 1.9–2.85(m, 4H), 3.98(s, 3H), 3.4–4.1(m, 4H), 5.11(s, 2H), 6.65–7.10(m, 4H), 7.25–7.8(m, 5H), 9.4(s, 1H).

The 4-formyl-4-(3-hydroxyphenyl)tetrahydropyran, used as a starting material, was obtained as follows:

A mixture of 4-(3-benzyloxyphenyl)-4-formyltetrahydropyran (1 g), 10% palladium-on-charcoal catalyst (0.15 g), ethyl acetate (10 ml) and ethanol (20 ml) was stirred under 2.7 atmospheres pressure of hydrogen for 16 hours. The mixture was filtered and the filtrate was evaporated. The residue was purified by column chromatography using initially methylene chloride and then a 20:3 v/v mixture of methylene chloride and diethyl ether as eluent. There was thus obtained the required starting material (0.162 g, 23%), m.p. 123°–124° C.

EXAMPLE 16

Using a similar procedure to that described in Example 14, 6-bromomethyl-1-methyl-1,2-dihydroquinolin-2-one was reacted with 4-acetyl-4-(3-hydroxyphenyl)-tetrahydropyran to give 4-acetyl-4-[3-(1-methyl-2-oxo-1,2-dihydroquinolin-6-ylmethoxy)phenyl]tetrahydropyran in 52% yield, m.p. 125°–126° C.

The 4-acetyl-4-(3-hydroxyphenyl)tetrahydropyran, used as a starting material, was obtained as follows:

The procedure described in the first paragraph of the portion of Example 14 which is concerned with the preparation of starting materials was repeated except that 4-(1-hydroxyethyl)-4-(3-hydroxyphenyl)tetrahydropyran was used in place of 4-(3-benzyloxyphenyl)-4-hydroxymethyltetrahydropyran. There was thus obtained the required starting material in 77% yield, m.p. 120°–121° C.

EXAMPLE 17

Using a similar procedure to that described in Example 14, 6-bromomethyl-1-methyl-1,2-dihydroquinolin-2-one was reacted with 4-(5-fluoro-3-hydroxyphenyl)-3,4,5,6-tetrahydro-2H-pyran to give 4-15-fluoro-3-(1-methyl-2-oxo-1,2-dihydroquinolin-6-ylmethoxy)-phenyl]-3,4,5,6-tetrahydro-2H-pyran in 46% yield, m.p. 126°–127° C.

The 4-(5-fluoro-3-hydroxyphenyl)-3,4,5,6-tetrahydro-2H-pyran, used as a starting material, was obtained as follows:

Sodium hydride (50% w/w dispersion in mineral oil, 2.11 g) was added portionwise to a stirred solution of 4-(3-benzyloxy-5-fluorophenyl)-4-hydroxytetrahydropyran (12.1 g) in THF (150 ml). The mixture was stirred at ambient temperature for 1 hour, cooled in an ice-bath and methyl iodide (3.75 ml) was added dropwise. The mixture was stirred at ambient temperature for 18 hours, 2N aqueous hydrochloric acid (3 drops) were added and the organic solvent was evaporated. The residue was partitioned between ethyl acetate and water. The organic phase was separated, washed with water and with brine, dried (MgSO$_4$) and evaporated. There was thus obtained 4-(3-benzyloxy-5-fluorophenyl)-4-methoxytetrahydropyran (12.5 g, 99%), as a pale yellow oil which was used without further purification.

A solution of the product so obtained in ethanol (100 ml) was hydrogenated in the presence of 10% palladium-on-charcoal catalyst for 3 hours. The mixture was filtered and the filtrate was evaporated. There was thus obtained 4-(5-fluoro-3-hydroxyphenyl)-4-methoxytetrahydropyran (7.7 g, 86%), m.p. 123°–124° C.

A saturated solution of hydrogen chloride in diethyl ether (1.5 ml) was added to a solution of a portion (0.678 g) of the product so obtained in methanol (15 ml). The mixture was heated to reflux for 20 hours. The mixture was evaporated and the residue was purified by column chromatography using a 2:1 v/v mixture of hexane and ethyl acetate as eluent. There was thus obtained 4-(5-fluoro-3-hydroxyphenyl)-3,6-dihydro-2H-pyran (0.417 g, 72%), m.p. 137°–138° C.

A mixture of a portion (0.334 g) of the product so obtained, 10% palladium-on-charcoal catalyst (0.065 g) and ethanol (15 ml) was stirred under an atmosphere of hydrogen for 7 hours. The mixture was filtered and the filtrate was evaporated. The residue was purified by column chromatography using diethyl ether as eluent.

There was thus obtained the required starting material (0.311 g, 92%), m.p. 128°–130° C.

EXAMPLE 18

Using a similar procedure to that described in Example 14, 6-bromomethyl-1-methyl-1,2-dihydroquinolin-2-one was reacted with 4-(3-hydroxyphenyl)-4-methyltetrahydropyran to give 4-methyl-4-[3-(1-methyl-2-oxo-1,2-dihydroquinolin-6-ylmethoxy)phenyl]tetrahydropyran in 40% yield, m.p. 107°–108° C.

The 4-(3-hydroxyphenyl)-4-methyltetrahydropyran, used as a starting material, was obtained as follows:

A mixture of iodine (1.91 g), imidazole (0.68 g), triphenylphosphine (1.97 g), acetonitrile (5 ml) and bis(2-methoxyethyl ether (15 ml) was stirred at ambient temperature for 1 hour. A solution of 4-(3-benzyloxyphenyl)-4-hydroxymethyltetrahydropyran (1.5 g) in acetonitrile (2 ml) was added and the mixture was heated to 110° C. for 6 hours. The mixture was evaporated and the residue was partitioned between ethyl acetate and an aqueous sodium dithionite solution (10% w/v). The organic phase was washed with water and with brine, dried (MgSO$_4$) and evaporated. The residue was purified by column chromatography using a 2:1 v/v mixture of petroleum ether (b.p. 40°–60° C.) and methylene chloride as eluent. There was thus obtained an oil which crystallised on trituration under pentane. There was thus obtained 4-(3-benzyloxyphenyl)-4-iodomethyltetrahydropyran (1.43 g, 70%), m.p. 77° C.

A mixture of a portion (0.58 g) of the product so obtained, triethylamine (0.395 ml), 10% palladium-on-charcoal catalyst (0.2 g) and ethyl acetate (6 ml) was stirred under 4.7 atmospheres pressure of hydrogen for 16 hours. The mixture was filtered and the filtrate was evaporated. The residue was purified by column chromatography using a 6:1 v/v mixture of petroleum ether (b.p. 40°–60° C.) and ethyl acetate as eluent. There was thus obtained 4-(3-benzyloxyphenyl)-4-methyltetrahydropyran (0.22 g, 55%), as an oil.

A mixture of the product so obtained, 10% palladium-on-charcoal catalyst (0.4 g) and ethanol (5 ml) was stirred under 4 atmospheres pressure of hydrogen for 5 hours. The mixture was filtered and the filtrate was evaporated. The residue was purified by column chromatography using a 10:1 v/v mixture of methylene chloride and diethyl ether as eluent. There was thus obtained the required starting material (0.14 g, 92%), m.p. 94°–95° C.

EXAMPLE 19

Using a similar procedure to that described in Example 14, 6-bromomethyl-1-methyl-1,2-dihydroquinolin-2-one was reacted with 4-ethyl-4-(3-hydroxyphenyl)tetrahydropyran to give 4-ethyl-4-[3-(1-methyl-2-oxo-1,2-dihydroquinolin-6-ylmethoxy)phenyl]tetrahydropyran in 63% yield, m.p. 139° C.

The 4-ethyl-4-(3-hydroxyphenyl)tetrahydropyran, used a starting material, was obtained as follows:

n-Butyl-lithium (1.6M in hexane, 1.375 ml) was added dropwise to a solution of methyltriphenylphosphonium bromide (0.786 g) in a mixture of THF (15 ml) and diethyl ether (2 ml). The mixture was stirred at ambient temperature for 2 hours. The solution so obtained was added dropwise to a solution of 4-(3-benzyloxyphenyl)-4-formyltetrahydropyran (0.592 g) in diethyl ether (10 ml) and the mixture was stirred at ambient temperature for 4 hours. The mixture was filtered and the filtrate was evaporated. The residue was purified by column chromatography using increasingly polar mixtures of petroleum ether (b.p 40°–60° C.) and ethyl acetate as eluent. There was thus obtained 4-(3-benzyloxyphenyl-4-vinyltetrahydropyran (0.407 g, 70%), as an oil.

A mixture of the product so obtained, 10% palladium-on-charcoal catalyst (0.05 g) and ethanol (5 ml) was stirred under 3 atmospheres pressure of hydrogen for 16 hours. The mixture was filtered and the filtrate was evaporated. The residue was purified by column chromatography using initially methylene chloride and then a 10:1 v/v mixture of methylene chloride and diethyl ether as eluent. There was thus obtained the required starting material (0.27 g, 96%), m.p. 64°–65° C.

EXAMPLE 20

Using a similar procedure to that described in Example 14, 6-bromomethyl-1-methyl-1,2-dihydroquinolin-2-one was reacted with (2RS,4RS)-4-ethyl-4-(5-fluoro-3-hydroxyphenyl)-2-methyltetrahydropyran to give (2RS,4RS)-4-ethyl-4-[5-fluoro-3-(1-methyl-2-oxo-1,2-dihydroquinolin-6-ylmethoxy)phenyl]-2-methyltetrahydropyran in 52% yield, m.p. 99° C.

The (2RS,4RS)-4-ethyl-4-(5-fluoro-3-hydroxyphenyl)-2-methyltetrahydropyran, used as a starting material, was obtained as follows:

A mixture of iodine (115.5 g), imidazole (41.2 g), triphenylphosphine (159 g), acetonitrile (200 ml) and diethyl ether (500 ml) was stirred at ambient temperature for 30 minutes. A solution of 2-methyl-3-oxapentane-1,5-diol (*J.C.S. Perkin I*, 1979, 1029; 18.2 g) in diethyl ether (20 ml) was added dropwise and the mixture was stirred at ambient temperature for 3 hours. The mixture was poured into petroleum ether (b.p. 40°–60° C., 3 liters). The organic solution was decanted from the residue which had been deposited. The organic solution was evaporated and the material so obtained was purified by column chromatography using initially petroleum ether (b.p. 40°–60° C.) and then a 10:1 v/v mixture of petroleum ether (b.p. 40°–60° C.) and methylene chloride as eluent. There was thus obtained 1,5-diiodo-2-methyl-3-oxapentane (30.3 g, 61%) as a liquid.

Sodium hydride (60% w/w dispersion in mineral oil, 9.17 g) was added portionwise to a solution of ethyl 3,5-difluorophenylacetate (17 g) in THF (400 ml) and the mixture was stirred at ambient temperature for 1 hour. A solution of 1,5-diiodo-2-methyl-3-oxapentane (30.3 g) in THF (20 ml) was added dropwise and the mixture was stirred at ambient temperature for 2 hours. The mixture was filtered and the filtrate was evaporated. The residue was purified by column chromatography using a 19:1 v/v mixture of petroleum ether (b.p. 40°–60° C.) and ethyl acetate as eluent. There was thus obtained, as a mixture of diastereoisomers, 4-ethoxycarbonyl-4-(3,5-difluorophenyl)-2-methyltetrahydropyran (16.5 g). The mixture of diastereoisomers was separated by further chromatography using a 10:1 v/v mixture of petroleum ether (b.p 40°–60° C.) and ethyl acetate as eluent. There was thus obtained:

a less polar isomer (7.75 g), the (2RS,4SR)-isomer, having the 2-methyl and 4-ethoxycarbonyl groups in a trans-relationship; and a more polar isomer (5.9 g), the (2RS,4RS)-isomer, having the 2-methyl an 4-ethoxycarbonyl groups in a cis-relationship.

Sodium hydride (60% w/w dispersion in mineral oil, 0.258 g) was added portionwise to a stirred solution of benzyl alcohol (0.582 g) in N-methylpyrrolidin-2-one (10 ml) and the mixture was stirred at ambient temperature for 45 minutes. A solution of a portion (1.53 g) of the less polar isomer obtained above in N-methylpyrrolidin-2-one (5 ml) was added and the mixture was stirred at ambient temperature for 1.5 hours and then heated to 50° C. for 1.5 hours. The mixture was partitioned between diethyl ether and water. The organic phase was washed with water and with brine, dried (MgSO₄) and evaporated. The residue was purified by column chromatography using a 10:1 v/v mixture of petroleum ether (b.p 40°-60° C.) and ethyl acetate as eluent. There was thus obtained (2RS,4SR)-4-(3-benzyloxy-5-fluorophenyl)-4-ethoxycarbonyl-2-methyltetrahydropyran (0.756 g, 45%), as an oil.

A solution of the material so obtained in diethyl ether (4 ml) was added to a stirred suspension of lithium aluminium hydride (0.07 g) in diethyl ether (10 ml) and the mixture was stirred at ambient temperature for 30 minutes. Water (5 ml) was added cautiously to destroy the excess of reducing agent. The mixture was extracted with diethyl ether. The organic phase was washed with water, dried (MgSO₄) and evaporated. The residue was purified by column chromatography using a 10:3 v/v mixture of petroleum ether (b.p. 40°-60° C.) and ethyl acetate as eluent. There was thus obtained (2RS,4SR)-4-(3-benzyloxy-5-fluorophenyl)-4-hydroxymethyl-2-methyltetrahydropyran (0.589 g, 89%), as an oil.

Using a similar procedure to that described in the first paragraph of the portion of Example 14 which is concerned with the preparation of starting materials, the 4-hydroxymethyltetrahydropyran so obtained was oxidised to give (2RS,4SR)-4-(3-benzyloxy-5-fluorophenyl)-4-formyl-2-methyltetrahydropyran (0.524 g, 91%), as an oil.

n-Butyl-lithium (1.6M in hexane, 1.16 ml) was added dropwise to a solution of methyltriphenylphosphonium bromide (0.664 g) in THF (10 ml) which had been cooled to −70° C. The mixture was stirred at −70° C. for 1 hours. A solution of the 4-formyltetrahydropyran so obtained in THF (2 ml) was added dropwise and the mixture was stirred at −70° C. for 30 minutes. The mixture was allowed to warm to ambient temperature. The mixture was filtered and the filtrate was evaporated. The residue was purified by column chromatography using methylene chloride as eluent. There was thus obtained (2RS,4RS)-4-(3-benzyloxy-5-fluorophenyl)-2-methyl-4-vinyltetrahydropyran (0.4 g, 79%), as an oil.

Using a similar procedure to that described in the last paragraph of the portion of Example 19 which is concerned with the preparation of starting materials, the 4-vinyltetrahydropyran so obtained was hydrogenated to give (2RS,4RS)-4-ethyl-4-(5-fluoro-3-hydroxyphenyl)-2-methyltetrahydropyran (0.26 g, 92%), as an oil.

NMR Spectrum (CDCl₃, δ values) 0.57(t, 3H), 1.20(d, 3H), 1.15-2.10(m, 6H), 3.5-4.1(m, 3H), 5.10(s, 1H), 6.3-6.7(m, 3H).

EXAMPLE 21

Using a similar procedure to that described in Example 14, 6-bromomethyl-1-methyl-1,2-dihydroquinolin-2-one was reacted with (2RS,4SR)-4-ethyl-4-(5-fluoro-3-hydroxyphenyl)-2-methyltetrahydropyran to give (2RS,4SR)-4-ethyl-4-[5-fluoro-3-(1-methyl-2-oxo-1,2-dihydroquinolin-6-ylmethoxy)phenyl]-2-methyltetrahydropyran in 68% yield, as a foam.

NMR Spectrum (CDCl₃, δ values) 0.5(t, 3H), 1.1(d, 3H), 1.1-2.2(m, 6H), 3.1-4.0(m, 6H), 5.05(s, 2H), 6.4-6.7(m, 4H), 7.2-7.7(m, 4H).

The (2RS,4SR)-4-ethyl-4-(5-fluoro-3-hydroxyphenyl)-2-methyltetrahydropyran, used as a starting material, was obtained as follows:

The procedures described in the last five paragraphs of the portion of Example 20 which is concerned with the preparation of starting materials were repeated except that the more polar diasteroisomer, i.e. (2RS,4SR)-4-ethoxycarbonyl-4-(3,5-difluorophenyl)-2-methyltetrahydropyran, was used in place of the less polar diastereoisomer. There was thus obtained the required starting material in 14% yield, as an oil.

NMR Spectrum (CDCl₃, δ values) 0.6(t, 3H), 1.15(d, 3H), 1.2-2.4(m, 6H), 3.25-4.0(m, 3H), 5.4(broad s, 1H), 6.3-6.6(m, 3H).

EXAMPLE 22

The following illustrate representative pharmaceutical dosage forms containing the compound of formula I, or a pharmaceutically-acceptable salt thereof (hereafter compound X), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph.Eur | 488.5 |
| Magnesium stearate | 1.5 |

| (e) Injection I | (50 mg/ml) |
|---|---|
| Compound X | 5.0% w/v |
| 1M Sodium hydroxide solution | 15.0% v/v |
| 0.1M Hydrochloric acid (to adjust pH to 7.6) | 4.5% w/v |
| Polyethylene glycol 400 | |
| Water for injection to 100% | |

| (f) Injection II | (10 mg/ml) |
|---|---|
| Compound X | 1.0% w/v |
| Sodium phosphate BP | 3.6% w/v |
| 0.1M Sodium hydroxide solution | 15.0% v/v |
| Water for injection to 100% | |

| (g) Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

| (h) Aerosol I | mg/ml |
|---|---|
| Compound X | 10.0 |
| Sorbitan trioleate | 13.5 |

-continued

| Trichlorofluoromethane | 910.0 |
| --- | --- |
| Dichlorodifluoromethane | 490.0 |

| (i) Aerosol II | mg/ml |
| --- | --- |
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
| --- | --- |
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| (k) Aerosol IV | mg/ml |
| --- | --- |
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

Note

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

CHEMICAL FORMULAE

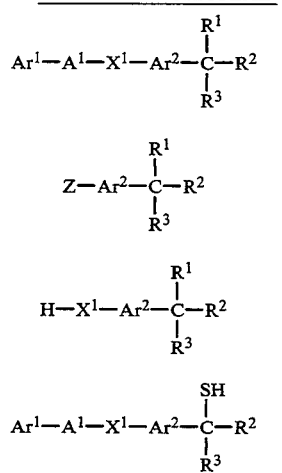

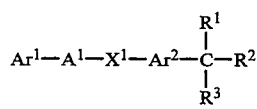

What we claim is:

1. A cyclic ether derivative of the formula I $$Ar^1-A^1-X^1-Ar^2-\underset{R^3}{\overset{R^1}{\underset{|}{\overset{|}{C}}}}-R^2 \qquad I$$

wherein $Ar^1$ is dihydroquinoline which may optionally bear up to five substituents selected from amino, halogeno, hydroxy, cyano, oxo, thioxo, (1-4C)alkyl, (1-4C)alkoxy, (1-4C)alkylthio, (1-4C)alkylsulphinyl, (1-4C)alkylsulphonyl, (1-4C)alkylamino, di-[(1-4C)alkyl]amino, (2-4C)alkanoyl, fluoro-(1-4C)alkyl, cyano-(1-4C)alkyl, phenyl, benzoyl and phenyl-(1-4C)alkyl, and wherein said phenyl, benzoyl or phenyl-(1-4C)alkyl substituents may optionally bear a substituent selected from halogeno, (1-4C)alkyl and (1-4C)alkoxy;

wherein $A^1$ is a direct link to or is (1-3C)alkylene;

wherein $X^1$ is oxy, thio, sulphinyl, sulphonyl or imino;

wherein $Ar^2$ is phenylene which may optionally bear one or two substituents selected from halogeno, hydroxy, amino, nitro, cyano carbamoyl, ureido, (1-4C)alkyl, (1-4C)alkoxy, (1-4C)alkylamino, di-[(1-4C)alkyl]amino, fluoro-(1-4C)alkyl and (2-4C)alkanoylamino;

wherein $R^1$ is (1-4C)alkylthio, (1-4C)alkylsulphinyl, (1-4C)alkylsulphonyl, (1-4C)alkylamino or di-[(1-4C)alkyl]amino, or $R^1$ is hydrogen, formyl, cyano, carbamoyl, (1-4C)alkyl, (1-4C)alkoxycarbonyl, N-(1-4C)alkylcarbamoyl, N,N-di-[(1-4C)alkyl]carbamoyl, hydroxy-(1-4C)alkyl, fluoro-(1-4C)alkylthio, (2-4C)alkanoyl or (1-4C)alkoxy-(1-4C)alkyl; and wherein $R^2$ and $R^3$ together form a group of the formula $-A^2-X^2-A^3-$ which, together with the carbon atom to which $A^2$ and $A^3$ are attached, defines a ring having 5 to 7 ring atoms, wherein $A^2$ and $A^3$, which may be the same or different, each is (1-3C)alkylene and $X^2$ is oxy, and which ring may bear one, two or three substituents, which may be the same or different, selected from hydroxy, (1-4C)alkyl and (1-4C)alkoxy;

or a pharmaceutically-acceptable salt thereof.

2. A cyclic ether derivative of the formula I as claimed in claim 1 wherein $Ar^1$ is dihydroquinoline which may optionally bear up to five substituents selected from amino, halogeno, hydroxy, cyano, oxo, thioxo, (1-4C)alkyl, (1-4C)alkoxy, (1-4C)alkylthio, (1-4C)alkylsulphinyl, (1-4C)alkylsulphonyl, (1-4C)alkylamino, di-[(1-4C)alkyl]amino, (2-4C)alkanoyl, fluoro-(1-4C)alkyl, cyano-(1-4C)alkyl, phenyl, benzoyl and phenyl-(1-4C)alkyl, and wherein said phenyl, benzoyl or phenyl-(1-4C)alkyl substituents may optionally bear a substituent selected from halogeno, (1-4C)alkyl and (1-4C)alkoxy;

wherein $A^1$ is a direct link to $X^1$ or is (1-3C)alkylene;

wherein $X^1$ is oxy, thio, sulphinyl, sulphonyl or imino;

wherein $Ar^2$ is phenylene which may optionally bear one or two substituents selected from halogeno, hydroxy, amino, nitro, cyano carbamoyl, ureido, (1-4C)alkyl, (1-4C)alkoxy, (1-4C)alkylamino, di-[(1-4C)alkyl]amino, fluoro-(1-4C)alkyl and (2-4C)alkanoylamino;

wherein $R^1$ is (1-4C)alkylthio, (1-4C)alkylsulphinyl, (1-4C)alkylsulphonyl, (1-4C)alkylamino or di-[(1-4C)alkyl]amino, or $R^1$ is cyano, carbamoyl, (1-4C)alkoxycarbonyl, N-(1-4C)alkylcarbamoyl, N,N-di-[(1-4C)alkyl]carbamoyl, hydroxy-(1-4C)alkyl or (1-4C)alkoxy-(1-4C)alkyl; and wherein $R^2$ and $R^3$ together form a group of the formula $-A^2-X^2-A^3-$ which, together with the carbon atom to which $A^2$ and $A^3$ are attached, defines a ring having 5 to 7 ring atoms, wherein $A^2$ and $A^3$, which may be the same or different, each is (1-3C)alkylene and $X^2$ is oxy, and which ring may bear one, two or three substituents, which may be the same or different, selected from hydroxy, (1-4C)alkyl and (1-4C)alkoxy;

or a pharmaceutically-acceptable salt thereof.

3. A cyclic ether derivative of the formula I as claimed in claim 1
wherein $Ar^1$ is 2-oxo-1,2-dihydroquinolin-3-yl, 2-oxo-1,2-dihydroquinolin-6-yl or 2-oxo-1,2-dihydroquinolin-7-yl, which may optionally bear one, two or three substituents selected from fluoro, chloro, methyl, ethyl, 2-fluoroethyl, phenyl and benzyl;

$A^1$ is a direct link to $X^1$, or is methylene;

$X^1$ is oxy, thio, sulphinyl or sulphonyl;

$Ar^2$ is 1,3-phenylene or 1,4-phenylene which may optionally bear one or two substituents selected from fluoro, chloro, hydroxy, amino, nitro, ureido, methoxy, dimethylamino, trifluoromethyl and acetamido;

$R^1$ is methylthio, ethylthio, propylthio, methylsulphinyl, ethylsulphinyl, propylsulphinyl, methylsulphonyl, ethylsulphonyl, propylsulphonyl, methylamino, ethylamino, dimethylamino or diethylamino, or $R^1$ is cyano, carbamoyl, methoxycarbonyl, ethoxycarbonyl, propoxycarbonyl, N-methylcarbamoyl, N-ethylcarbamoyl, N,N-dimethylcarbamoyl, N,N-diethylcarbamoyl, hydroxymethyl, 2-hydroxyethyl, 3-hydroxypropyl, methoxymethyl, ethoxymethyl, 2-methoxyethyl, 2-ethoxyethyl, 3-methoxypropyl or 3-ethoxypropyl; and $R^2$ and $R^3$ together form a group of the formula $-A^2-X^2-A^3-$ which, together with the carbon atom to which $A^2$ and $A^3$ are attached, defines a ring having 5 or 6 ring atoms, wherein $A^2$ is ethylene, $A^3$ is methylene or ethylene, and $X^2$ is oxy, and which ring may bear one or two substituents selected from methyl and ethyl;

or a pharmaceutically-acceptable salt thereof.

4. A cyclic ether derivative of the formula I as claimed in claim 1 wherein $Ar^1$ is 2-oxo-1,2-dihydroquinolin-6-yl which may optionally bear one or two substituents selected from fluoro, chloro, methyl and ethyl;

$A^1$ is a direct link to $X^1$, or is methylene;

$X^1$ is oxy, thio, sulphinyl or sulphonyl;

$Ar^2$ is 1,3-phenylene which may optionally bear a substituent selected from fluoro, chloro and trifluoromethyl;

$R^1$ is methylthio, ethylthio, propylthio, isopropylthio, tert-butylthio, methylsulphinyl, ethylsulphinyl, propylsulphinyl, hydrogen, formyl, cyano, methoxycarbonyl, ethoxycarbonyl, propoxycarbonyl, hydroxymethyl, 1-hydroxyethyl, 2-hydroxyethyl, 2,2,2-trifluoroethylthio, acetyl, propionyl, methoxymethyl, ethoxymethyl or 2-methoxyethyl; and $R^2$ and $R^3$ together form a group of the formula $-A^2-X^2-A^3-$ which, together with the carbon atom to which each of $A^2$ and $A^3$ is attached, defines a ring having 5 or 6 ring atoms, and $X^2$ is oxy, and which ring may bear one or two substituents selected from methyl and ethyl; or a pharmaceutically-acceptable salt thereof.

5. A cyclic ether derivative of the formula I as claimed in claim 1 wherein $Ar^1$ is 1-methyl-2-oxo-1,2-dihydroquinolin-6-yl;

$A^1$ is methylene and $X^1$ is oxy;

$Ar^2$ is 1,3-phenylene or 5-fluoro-1,3-phenylene;

$R^1$ is methylthio, ethylthio, isopropylthio, tert-butylthio, methylsulphinyl, hydrogen, formyl, cyano, methyl, ethyl, ethoxycarbonyl, hydroxymethyl, 1-hydroxyethyl, 2,2,2-trifluoroethylthio, acetyl or methoxymethyl; and $R^2$ and $R^3$ together form a group of the formula $-A^2-X^2-A^3-$ which, together with the carbon atom to which each of $A^2$ and $A^3$ is attached, defines a ring having 6 ring atoms, wherein $A^2$ is ethylene, $A^3$ is ethylene and $X^2$ is oxy, and which ring may bear a methyl substituent alpha to $X^2$;

or a pharmaceutically-acceptable salt thereof.

6. A cyclic ether derivative of the formula I, or a pharmaceutically-acceptable salt thereof as defined in claim 1, being 4-ethoxycarbonyl-4-[3-(1-methyl-2-oxo-1,2-dihydroquinolin-6-ylmethoxy)phenyl]tetrahydropyran.

7. A cyclic ether derivative of the formula I, or a pharmaceutically-acceptable salt thereof as defined in claim 1, selected from the group consisting of:

4-acetyl-4-[3-(1-methyl-2-oxo-1,2-dihydroquinolin-6-ylmethoxy)phenyl]tetrahydropyran, 4-[5-fluoro-3-(1-methyl-2-oxo-1,2-dihydroquinolin-6-ylmethoxy)phenyl]-3,4,5,6-tetrahydro-2H-pyran, 4-ethyl-4-3-(1-methyl-2-oxo-1,2-dihydroquinolin-6-ylmethoxy)phenyl]tetrahydropyran, (2RS,4RS)-4-ethyl-4-[5-fluoro-3-(1-methyl-2-oxo-1,2-dihydroquinolin-6-ylmethoxy)phenyl]-2-methyltetrahydropyran and 4-[5-fluoro-3-(1-methyl-2-oxo-1,2-dihydroquinolin-6-ylmethoxy)phenyl]-4-methylthiotetrahydropyran.

8. A pharmaceutical composition which comprises a cyclic ether derivative of the formula I, or a pharmaceutically-acceptable salt thereof, as claimed in any one of claims 1 to 2 and 3 to 7 in association with a pharmaceutically-acceptable diluent or carrier.

9. A method of treating a disease or medical condition mediated alone or in part by one or more leukotrienes which comprises administering to a warm-blooded animal requiring such treatment an effective amount of a cyclic ether derivative of the formula I, or a pharmaceutically-acceptable salt thereof, as claimed in any one of claims 1 to 2 and 3 to 7.

* * * * *